(12) United States Patent
Andersen

(10) Patent No.: US 12,165,312 B2
(45) Date of Patent: Dec. 10, 2024

(54) OSTOMY CONDITION CLASSIFICATION WITH MASKING, DEVICES AND RELATED METHODS

(71) Applicant: Coloplast A/S, Humlebaek (DK)

(72) Inventor: Niels Kristian Mäkinen Andersen, Glostrup (DK)

(73) Assignee: Coloplast A/S, Humlebaek (DK)

( * ) Notice: Subject to any disclaimer, the term of this patent is extended or adjusted under 35 U.S.C. 154(b) by 586 days.

(21) Appl. No.: 17/415,752

(22) PCT Filed: Dec. 19, 2019

(86) PCT No.: PCT/DK2019/050415
§ 371 (c)(1),
(2) Date: Jun. 18, 2021

(87) PCT Pub. No.: WO2020/125906
PCT Pub. Date: Jun. 25, 2020

(65) Prior Publication Data
US 2022/0108440 A1    Apr. 7, 2022

(30) Foreign Application Priority Data

Dec. 20, 2018    (DK) .................. PA 2018 70831

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/1032* (2013.01); *A61B 5/445* (2013.01);
(Continued)

(58) Field of Classification Search
CPC ............... G06T 7/0012; G06T 7/90; G06T 2207/20084; A61B 5/1032; A61B 5/445;
(Continued)

(56) References Cited

U.S. PATENT DOCUMENTS 2,327,514 A    8/1943    Fenwick
2,542,233 A    2/1951    Carroll
(Continued)

FOREIGN PATENT DOCUMENTS

CA    2540756 C    1/2008
CA    3009449 C    9/2019
(Continued)

*Primary Examiner* — Santiago Garcia
(74) *Attorney, Agent, or Firm* — Coloplast Corp., Coloplast A/S; Nick Baumann

(57) ABSTRACT

A method for classifying an ostomy condition, the method comprising: obtaining image data, the image data comprising stoma image data of a stomal area including a stoma and/or appliance image data of an adhesive surface of an ostomy appliance; determining one or more image representations based on the image data; determining one or more ostomy representations including a first ostomy parameter based on the one or more image representations; and outputting the first ostomy parameter.

20 Claims, 9 Drawing Sheets

(51) Int. Cl.
*A61B 5/103* (2006.01)
*G06T 7/90* (2017.01)
*G06V 10/764* (2022.01)

(52) U.S. Cl.
CPC .............. *A61B 5/7264* (2013.01); *G06T 7/90* (2017.01); *G06V 10/764* (2022.01); *G06T 2207/20084* (2013.01)

(58) Field of Classification Search
CPC ... A61B 5/7264; A61B 5/0036; A61B 5/0077; A61B 5/42; A61B 5/4851; G06V 10/764; A61F 5/445
See application file for complete search history.

(56) References Cited

U.S. PATENT DOCUMENTS

| | | |
|---|---|---|
| 2,544,579 A | 3/1951 | Ardner |
| 3,214,502 A | 10/1965 | Schaar |
| 3,808,354 A | 4/1974 | Feezor et al. |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,519,644 A | 5/1996 | Benton |
| 5,570,082 A | 10/1996 | Mahgerefteh et al. |
| 5,593,397 A | 1/1997 | La Gro |
| 5,626,135 A | 5/1997 | Sanfilippo |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries et al. |
| 5,834,009 A | 11/1998 | Sawers et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,078,261 A | 6/2000 | Davsko |
| 6,103,033 A | 8/2000 | Say et al. |
| 6,135,986 A | 10/2000 | Leisner et al. |
| 6,171,289 B1 | 1/2001 | Millot et al. |
| 6,206,864 B1 | 3/2001 | Kavanagh et al. |
| 6,241,704 B1 | 6/2001 | Peterson et al. |
| 6,270,445 B1 | 8/2001 | Dean, Jr. et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | Von et al. |
| 6,520,943 B1 | 2/2003 | Wagner |
| 6,677,859 B1 | 1/2004 | Bensen |
| 6,764,474 B2 | 7/2004 | Nielsen et al. |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,326,051 B1 | 12/2012 | Hobbs |
| 8,398,575 B1 | 3/2013 | McCall |
| 8,398,603 B2 | 3/2013 | Thirstrup et al. |
| 8,399,732 B2 | 3/2013 | Oelund et al. |
| 8,409,158 B2 | 4/2013 | Edvardsen et al. |
| 8,449,471 B2 | 5/2013 | Tran |
| 8,500,718 B2 | 8/2013 | Locke et al. |
| 8,632,492 B2 | 1/2014 | Delegge |
| 8,680,991 B2 | 3/2014 | Tran |
| 8,684,982 B2 | 4/2014 | Nguyen-Demary et al. |
| 8,740,865 B2 | 6/2014 | Krystek et al. |
| 8,795,257 B2 | 8/2014 | Coulthard et al. |
| 8,821,464 B2 | 9/2014 | Hanuka et al. |
| 8,975,465 B2 | 3/2015 | Hong et al. |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,566,383 B2 | 2/2017 | Yodfat et al. |
| 9,629,964 B2 | 4/2017 | Wuepper |
| 9,675,267 B2 | 6/2017 | Laakkonen et al. |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,426,342 B2 | 10/2019 | Hresko et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,238,133 B1 | 2/2022 | Brewer et al. |
| 11,306,224 B2 | 4/2022 | Chatterjee et al. |
| 11,406,525 B2 | 8/2022 | Seres et al. |
| 11,471,318 B2 | 10/2022 | Hansen et al. |
| 11,612,512 B2 | 3/2023 | Hansen et al. |
| 2001/0041920 A1 | 11/2001 | Starkweather et al. |
| 2001/0051787 A1 | 12/2001 | Haller et al. |
| 2002/0013613 A1 | 1/2002 | Haller et al. |
| 2002/0019615 A1 | 2/2002 | Roe et al. |
| 2002/0109621 A1 | 8/2002 | Khair et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |

(56) References Cited

U.S. PATENT DOCUMENTS

| | | |
|---|---|---|
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0256545 A1 | 11/2005 | Koh et al. |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2007/0204691 A1 | 9/2007 | Bogner et al. |
| 2008/0038536 A1 | 2/2008 | Strobech et al. |
| 2008/0041792 A1 | 2/2008 | Crnkovich et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0300578 A1 | 12/2008 | Freedman |
| 2008/0306459 A1 | 12/2008 | Albrectsen |
| 2009/0012501 A1 | 1/2009 | Boehringer et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0234916 A1 | 9/2009 | Cosentino et al. |
| 2009/0247970 A1 | 10/2009 | Keleny et al. |
| 2009/0264957 A1 | 10/2009 | Giftakis et al. |
| 2010/0010460 A1 | 1/2010 | Butler |
| 2010/0030167 A1 | 2/2010 | Thirstrup et al. |
| 2010/0072271 A1 | 3/2010 | Thorstensson |
| 2010/0106220 A1 | 4/2010 | Ecker et al. |
| 2010/0114047 A1 | 5/2010 | Song et al. |
| 2010/0271212 A1 | 10/2010 | Page |
| 2010/0311167 A1 | 12/2010 | Wood et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2011/0245682 A1 | 10/2011 | Robinson et al. |
| 2011/0246983 A1 | 10/2011 | Brunet et al. |
| 2011/0257496 A1 | 10/2011 | Terashima et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0283678 A1 | 11/2012 | Nguyen-Demary et al. |
| 2012/0304767 A1 | 12/2012 | Howard et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0078912 A1 | 3/2013 | San Vicente et al. |
| 2013/0086217 A1 | 4/2013 | Price et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0128815 A1 | 5/2014 | Cabiri et al. |
| 2014/0200426 A1 | 7/2014 | Taub et al. |
| 2014/0200538 A1 | 7/2014 | Euliano et al. |
| 2014/0236111 A1* | 8/2014 | Casado .............. G06F 3/00 |
| | | 604/332 |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0057634 A1 | 2/2015 | Mastrototaro et al. |
| 2015/0150457 A1 | 6/2015 | Wu et al. |
| 2015/0151051 A1 | 6/2015 | Tsoukalis |
| 2015/0230706 A1 | 8/2015 | Nakagawa et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0328389 A1 | 11/2015 | Heppe |
| 2015/0342777 A1 | 12/2015 | Seres et al. |
| 2015/0374896 A1 | 12/2015 | Du et al. |
| 2016/0008182 A1 | 1/2016 | Prokopuk et al. |
| 2016/0058604 A1* | 3/2016 | Wiltshire .............. A61F 5/4404 |
| | | 604/335 |
| 2016/0084869 A1 | 3/2016 | Yuen et al. |
| 2016/0103966 A1 | 4/2016 | Mirza |
| 2016/0117062 A1 | 4/2016 | Hussam et al. |
| 2016/0158056 A1 | 6/2016 | Davis et al. |
| 2016/0158517 A1 | 6/2016 | Nebbia |
| 2016/0158969 A1 | 6/2016 | McLane et al. |
| 2016/0166438 A1 | 6/2016 | Rovaniemi |
| 2016/0178387 A1 | 6/2016 | Yamasaki et al. |
| 2016/0218555 A1 | 7/2016 | Slaby et al. |
| 2016/0235581 A1 | 8/2016 | Keleny et al. |
| 2016/0242654 A1 | 8/2016 | Quinlan et al. |
| 2016/0278990 A1 | 9/2016 | Chen |
| 2016/0305776 A1 | 10/2016 | Mrtensson et al. |
| 2016/0310140 A1 | 10/2016 | Belson et al. |
| 2016/0310329 A1 | 10/2016 | Patel et al. |
| 2016/0331232 A1 | 11/2016 | Love et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079576 A1 | 3/2017 | Stroebech et al. |
| 2017/0098044 A1 | 4/2017 | Lai et al. |
| 2017/0113001 A1 | 4/2017 | Trock |
| 2017/0140103 A1 | 5/2017 | Angelides |
| 2017/0156920 A1 | 6/2017 | Hunt et al. |
| 2017/0181628 A1 | 6/2017 | Burnette et al. |
| 2017/0340474 A1 | 11/2017 | Thirstrup et al. |
| 2017/0340498 A1 | 11/2017 | Tessmer et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2018/0049667 A1 | 2/2018 | Heppe |
| 2018/0055359 A1 | 3/2018 | Shamim et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0298240 A1 | 10/2018 | Chatterjee et al. |
| 2018/0318475 A1 | 11/2018 | Thomson et al. |
| 2019/0008439 A1 | 1/2019 | Sageder et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |

(56) References Cited

U.S. PATENT DOCUMENTS

| | | |
|---|---|---|
| 2020/0100931 A1 | 4/2020 | Schoess et al. |
| 2020/0188161 A1* | 6/2020 | Seres .................... G01K 13/00 |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0279368 A1* | 9/2020 | Tada .................. A61B 1/00016 |
| 2020/0297244 A1 | 9/2020 | Brownhill et al. |
| 2020/0306074 A1 | 10/2020 | Speiermann et al. |
| 2020/0322793 A1 | 10/2020 | Yang |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1 | 12/2020 | Sullivan et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0370217 A1 | 12/2021 | Kirschman |
| 2021/0386368 A1 | 12/2021 | Carlsson et al. |
| 2022/0000652 A1 | 1/2022 | Thirstrup et al. |
| 2022/0031227 A1* | 2/2022 | Cho ........................ G06V 10/82 |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0110585 A1* | 4/2022 | Andersen ............. A61B 5/7264 |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0145670 A1 | 5/2023 | Seres et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0329893 A1 | 10/2023 | Olsen et al. |
| 2023/0338005 A1 | 10/2023 | Barthe et al. |

FOREIGN PATENT DOCUMENTS

| | | |
|---|---|---|
| CA | 3002372 C | 3/2021 |
| CA | 2947016 C | 2/2023 |
| CN | 103269668 A | 8/2013 |
| CN | 203786580 U | 8/2014 |
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| CN | 105615896 B | 5/2019 |
| CN | 105359167 B | 6/2019 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0850076 B1 | 4/2005 |
| EP | 1188157 B1 | 12/2005 |
| EP | 2108345 A1 | 10/2009 |
| EP | 2489561 A2 | 8/2012 |
| EP | 2654646 A2 | 10/2013 |
| EP | 2453851 B1 | 10/2014 |
| EP | 3064179 A1 | 9/2016 |
| EP | 3213727 A1 | 9/2017 |
| GB | 2219679 A | 12/1989 |
| GB | 2225951 A | 6/1990 |
| GB | 2343628 A | 5/2000 |
| GB | 2465742 A | 6/2010 |
| GB | 2542093 A | 3/2017 |
| JP | 04-074882 A | 3/1992 |
| JP | 06-152077 A | 5/1994 |
| JP | 09-010184 A | 1/1997 |
| JP | 11-128352 A | 5/1999 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2014-033745 A | 2/2014 |
| JP | 2014-054368 A | 3/2014 |
| JP | 2014-507182 A | 3/2014 |
| KR | 10-2012-0003987 A | 1/2012 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2005/038693 A1 | 4/2005 |

(56) References Cited

FOREIGN PATENT DOCUMENTS

| | | |
|---|---|---|
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/098762 A1 | 9/2007 |
| WO | 2007/133555 A2 | 11/2007 |
| WO | 2007128038 A1 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012/084987 A2 | 6/2012 |
| WO | 2013/013197 A1 | 1/2013 |
| WO | 2013095231 A1 | 6/2013 |
| WO | 2014/004207 A1 | 1/2014 |
| WO | 2014/086369 A1 | 6/2014 |
| WO | 2015/007284 A1 | 1/2015 |
| WO | 2015/014774 A1 | 2/2015 |
| WO | 2015/094064 A1 | 6/2015 |
| WO | 2015084462 A1 | 6/2015 |
| WO | 2015/187366 A1 | 12/2015 |
| WO | 2016/132738 A1 | 8/2016 |
| WO | 2016/166731 A1 | 10/2016 |
| WO | 2016162038 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017108109 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/094635 A1 | 5/2019 |
| WO | 2019/120432 A1 | 6/2019 |
| WO | 2019/161859 A1 | 8/2019 |
| WO | 2019/161860 A1 | 8/2019 |
| WO | 2019/161863 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

\* cited by examiner

OSTOMY CONDITION CLASSIFICATION WITH MASKING, DEVICES AND RELATED METHODS

The disclosure relates to methods and devices for classification of an ostomy condition, and in particular for image-based classification of an ostomy condition.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
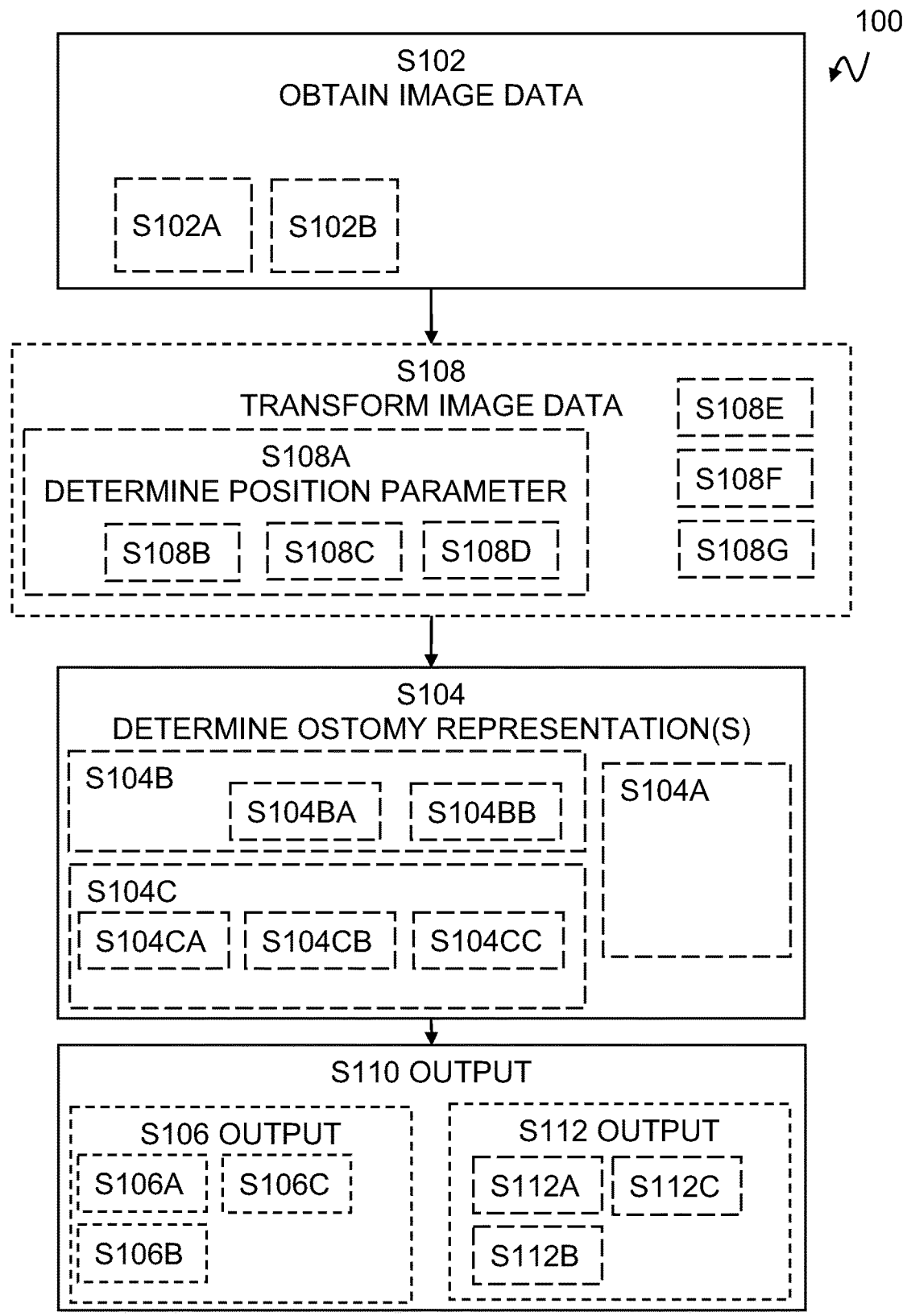
FIG. 1 illustrates an exemplary method according to the disclosure

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout the present disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

Throughout the present disclosure, the term "stomal area" denotes the stoma and an area around the stoma (peristomal area). The "peristomal area" denotes the area around the stoma covered by the adhesive surface when the ostomy appliance is attached to the skin of the user in its intended position during use.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to methods, devices, ostomy system, and devices thereof and in particular methods and devices for classifying an ostomy condition. The ostomy system comprises one or more of an ostomy appliance and one or more accessory devices. An accessory device (also referred to as an external device) may be a mobile phone (e.g. a smartphone), tablet computer, or other handheld device. An accessory device may be a personal electronic device, e.g. a wearable, such as a watch or other wrist-worn electronic device. The ostomy system may comprise a server device. The server device may be operated and/or controlled by the ostomy appliance manufacturer and/or a service centre.

A method for classifying an ostomy condition is provided, the method comprising obtaining image data, e.g. with an accessory device, the image data optionally comprising stoma image data of a stomal area including a stoma and/or appliance image data of an adhesive surface of an ostomy appliance; determining one or more ostomy representations, optionally including a first ostomy representation and/or a first ostomy parameter, based on the image data, such as based on the stoma image data and/or the appliance image data, and/or based on transformed image data; and outputting a first ostomy representation and/or the first ostomy parameter. The method optionally comprises transforming the image data. Determining the one or more ostomy representations based on the image data optionally comprises determining the first ostomy representation and/or the first ostomy parameter based on the image data and/or the transformed image data.

It is an advantage of the present disclosure that improved classification of ostomy condition is provided by compensating for image data of poor quality, e.g. image data obtained from different positions. Further, an improved classification of ostomy condition is provided by securing a uniform handling and/or interpretation of image data.

Also, it is an important advantage of the present disclosure that a more accurate classification of ostomy condition is provided by determining ostomy parameters in a uniform way. Further, the present disclosure allows for improved resolution in classifying an ostomy condition, e.g. resulting in classifying an ostomy condition into a larger number of ostomy condition types.

One or more exemplary methods for classifying an ostomy condition comprises:
 obtaining image data, the image data comprising stoma image data of a stomal area including a stoma and/or appliance image data of an adhesive surface of an ostomy appliance;
 determining one or more image representations based on the image data;
 determining one or more ostomy representations including a first ostomy parameter based on the one or more image representations; and
 outputting the first ostomy parameter and/or one or more ostomy representations.

One or more exemplary methods for classifying an ostomy condition comprises:
 obtaining image data, the image data comprising stoma image data of a stomal area including a stoma and/or appliance image data of an adhesive surface of an ostomy appliance;
 determining one or more ostomy representations including a first ostomy parameter, based on the image data; and
 outputting the first ostomy parameter and/or one or more ostomy representations, wherein the method comprises transforming the image data, and wherein determining the one or more ostomy representations based on the image data comprises determining the first ostomy parameter based on the transformed image data.

The method comprises obtaining image data, such as stoma image data and/or appliance image data. In one or more exemplary methods, obtaining image data may comprise capturing image data with a camera and transmitting the image data to a server device. In one or more exemplary methods, obtaining image data may comprise receiving, at a server device, the image data.

The method optionally comprises transforming the image data. In one or more exemplary methods, transforming the image data comprises transforming the image data with server device or with accessory device. Transforming the image data may comprise transmitting the transformed image data or parts thereof to server device. Transforming the image data may comprise receiving, in server device, the transformed image data or parts thereof.

The method comprises determining one or more ostomy representations, e.g. with accessory device and/or server device. Determining one or more ostomy representations may comprise receiving, with the accessory device, the one or more ostomy representations from server device.

In one or more exemplary methods, determining one or more ostomy representations including a first ostomy parameter based on the image data comprises:
 determining one or more image representations based on the image data; and determining one or more ostomy representations including a first ostomy parameter based on the one or more image representations.

In one or more exemplary methods, determining one or more ostomy representations including a first ostomy parameter based on the image data comprises:
 transforming the image data;
 determining one or more image representations based on the transformed image data; and
 determining one or more ostomy representations including a first ostomy parameter based on the one or more image representations.

An image representation may be a binary mask. Accordingly, the one or more image representations may be a binary mask. In other words, determining one or more ostomy representations may comprise determining one or more binary masks based on the image data or the transformed image data. In one or more exemplary methods, determining one or more image representations based on the image data are performed by convolutional neural network with N layers, e.g. in the range from 10-50 layers.

The method may comprise storing the one or more image representations, optionally including a stoma identifier and/or a user identifier.

In one or more exemplary methods and/or devices, the one or more image representations comprises a stoma background image representation, e.g. based on stoma image data and/or transformed stoma image data. The stoma background image representation is indicative of a background of the stoma image data, i.e. which part(s)/pixels of the stoma image data that are regarded or identified as background (e.g. including part of user skin not covered by adhesive surface of ostomy appliance). Determining one or more ostomy representations, such as the first ostomy representation and/or a third ostomy representation, may be based on the stoma background image representation. The stoma background image representation may have a resolution of 256×256 pixels or more, such as 512×512 pixels.

In one or more exemplary methods and/or devices, the one or more image representations comprises an appliance background image representation, e.g. based on appliance image data and/or transformed appliance image data. The appliance background image representation is indicative of a background of the appliance image data, i.e. which part(s)/pixels of the appliance image data that are regarded or identified as background (e.g. image part(s)/pixel(s) outside the area of the adhesive surface of htre ostomy appliance). Determining one or more ostomy representations, such as the second ostomy representation and/or a third ostomy representation, may be based on the appliance background image representation.

In one or more exemplary methods and/or devices, the one or more image representations comprises a stoma image representation, e.g. based on stoma image data and/or transformed stoma image data. The stoma image representation is indicative of the stoma, i.e. which part(s)/pixels of the ostomy image data that are regarded or identified as the stoma. Determining one or more ostomy representations, such as the first ostomy representation and/or a third ostomy representation, may be based on the stoma image representation. The stoma image representation may have a resolution of 256×256 pixels or more, such as 512×512 pixels.

In one or more exemplary methods and/or devices, the one or more image representations comprises a normal skin image representation, e.g. based on stoma image data and/or transformed stoma image data. The normal skin image representation is indicative of the normal skin of the peristomal area, i.e. which part(s)/pixels of the ostomy image data that are regarded or identified as not having discoloration. Determining one or more ostomy representations, such as the first ostomy representation and/or a third ostomy representation, may be based on the normal skin image representation. The normal skin image representation may have a resolution of 256×256 pixels or more, such as 512×512 pixels.

In one or more exemplary methods and/or devices, the one or more image representations comprises one or more, such as two, three, four or more, stoma discoloration representations. A stoma discoloration representation may be indicative of a discoloration of the peristomal area, i.e. which part(s)/pixels of the ostomy image data that are regarded or identified as the peristomal area and discoloured. A stoma discoloration representation may have a resolution of 256×256 pixels or more, such as 512×512 pixels.

In one or more exemplary methods and/or devices, the one or more image representations comprises a first stoma discoloration representation, e.g. based on stoma image data and/or transformed stoma image data. The first stoma discoloration representation may be indicative of a first discoloration of the peristomal area, i.e. which part(s)/pixels of the ostomy image data that are regarded or identified as the peristomal area and have a first discoloration (e.g. first degree of redness). The first stoma discoloration representation may be indicative of part(s)/pixels of the ostomy image data within the peristomal area having a color parameter, such as the red channel of an RGB image, within a first range or less than a first threshold, such as less than 0.25. The first stoma discoloration representation may be indicative of part(s)/pixels of the peristomal area with little or no discoloration. Determining one or more ostomy representations may be based on the first stoma discoloration representation.

In one or more exemplary methods and/or devices, the method comprises determining the first stoma discoloration representation based on red channel data of the image data/stoma image data.

In one or more exemplary methods and/or devices, the one or more image representations comprises a second stoma discoloration representation, e.g. based on stoma image data and/or transformed stoma image data. The second stoma discoloration representation may be indicative of a second discoloration of the peristomal area, i.e. which part(s)/pixels of the ostomy image data that are regarded or identified as the peristomal area and have a second discoloration (e.g. second degree of redness). The second discoloration is different from the first discoloration. The second stoma discoloration representation may be indicative of part(s)/pixels of the ostomy image data within the peristomal area having a color parameter, such as the red channel of an RGB image, within a second range, e.g. in the range from 0.25 to 0.5. The second stoma discoloration representation may be indicative of part(s)/pixels of the peristomal area with small, medium or high discoloration depending on the values of the second range. Determining one or more ostomy representations may be based on the second stoma discoloration representation.

In one or more exemplary methods and/or devices, the method comprises determining the second stoma discoloration representation based on red channel data of the image data/stoma image data.

In one or more exemplary methods and/or devices, the one or more image representations comprises a third stoma discoloration representation, e.g. based on stoma image data and/or transformed stoma image data. The third stoma discoloration representation may be indicative of a third discoloration of the peristomal area, i.e. which part(s)/pixels of the ostomy image data that are regarded or identified as the peristomal area and have a third discoloration (e.g. third degree of redness). The third stoma discoloration representation may be indicative of part(s)/pixels of the ostomy image data within the peristomal area having a color parameter, such as the red channel of an RGB image, within a third range, e.g. in the range from 0.5 to 0.75. The third stoma discoloration representation may be indicative of part(s)/pixels of the peristomal area with medium or high discoloration. Determining one or more ostomy representations may be based on the third stoma discoloration representation.

In one or more exemplary methods and/or devices, the method comprises determining the third stoma discoloration representation based on red channel data of the image data/stoma image data.

In one or more exemplary methods and/or devices, the one or more image representations comprises a fourth stoma discoloration representation, e.g. based on stoma image data and/or transformed stoma image data. The fourth stoma discoloration representation may be indicative of a fourth discoloration of the peristomal area, i.e. which part(s)/pixels of the ostomy image data that are regarded or identified as the peristomal area and have a fourth discoloration (e.g. fourth degree of redness). The fourth stoma discoloration representation may be indicative of part(s)/pixels of the ostomy image data within the peristomal area having a color parameter, such as the red channel of an RGB image, within a fourth range, e.g. in the range from 0.75 to 1, or larger than a fourth threshold. The fourth stoma discoloration representation may be indicative of part(s)/pixels of the peristomal area with high discoloration. Determining one or more ostomy representations may be based on the fourth stoma discoloration representation.

In one or more exemplary methods, the method comprises determining the fourth stoma discoloration representation based on red channel data of the image data/stoma image data.

In one or more exemplary methods, determining one or more image representations based on the image data comprises determining a base color parameter, e.g. including a first base color parameter and/or a second base color parameter, and determining the one or more image representations and/or one or more ostomy parameters based on the base color parameter. The base color parameter may be based on red channel data of the ostomy image data.

In one or more exemplary methods, determining one or more image representations and/or transforming image data optionally comprises applying an image conversion to the image data, such as the stoma image data. The image conversion may be based on one or more color channels including the red channel R and optionally the blue channel and/or the green channel of the image being converted. The converted image I_C may be given as:

$$I\_C = \text{Abs}(R - \text{Average}(G - B)),$$

where R is the red channel in the image, G is the green channel and B is the blue channel. In other words, the red, blue, and green channels of the image may be converted into a single combined channel also denoted CC for each pixel of the image. The converted image I_C may be a linear combination of the red, blue, and green channels.

In one or more exemplary methods, determining second ostomy parameter(s) may be based on the first base color parameter and/or the second base color parameter.

In one or more exemplary methods, a first base color parameter is indicative of a lower discoloration limit (i.e. corresponding to a discoloration of 0%) and optionally corresponding to a minimum of discoloration of pixels in the fourth stoma image representation (a first discoloration representation indicative of a discoloration of the peristomal area). The first base color parameter may correspond to an R or CC pixel value of 0 or the lowest R or CC pixel value in the (converted) image. The first base color parameter may be based on the CC value of pixels in the stoma image data identified as normal skin, e.g. for pixels near and outside a first boundary line indicative of a circumference or edge of the stomal area. Thus, the color of skin not being covered by adhesive may be used as a reference or baseline for no discoloration.

In one or more exemplary methods, a second base color parameter is indicative of an upper discoloration limit (i.e. corresponding to a pixel discoloration of 100%) and optionally corresponding to a maximum red channel pixel value or a maximum combined channel pixel value in the second stoma image representation (stoma image representation indicative of the stoma). Thus, the color of the stoma (which is always red) may be used as a reference color, in turn providing more uniform results and accommodating differences in light conditions when obtaining image data.

In one or more exemplary methods and/or devices, the one or more image representations comprises one or more, such as two, three, four or more, appliance discoloration representations. An appliance discoloration representation may be indicative of a discoloration of the adhesive surface of the ostomy appliance, i.e. which part(s)/pixels of the appliance image data that are regarded or identified as the adhesive surface and discoloured. An appliance discoloration representation may have a resolution of 256×256 pixels or more, such as 512×512 pixels.

The one or more image representations may comprise a first appliance discoloration representation, e.g. based on appliance image data and/or transformed appliance image data. The first appliance discoloration representation may be indicative of a first discoloration of the adhesive surface of the ostomy appliance, i.e. which part(s)/pixels of the appliance image data that are regarded or identified as the adhesive surface and have a first discoloration (e.g. first degree of output or simply output). The first appliance discoloration representation may be indicative of part(s)/pixels of the appliance image data having a color parameter, such as the red channel and/or the green channel of an RGB image, within a first range or less than a first threshold, such as less than 0.25. The first appliance discoloration representation may be indicative of part(s)/pixels of the adhesive surface with little or medium discoloration. Determining one or more ostomy representations may be based on the first appliance discoloration representation.

The one or more image representations may comprise a second appliance discoloration representation, e.g. based on appliance image data and/or transformed appliance image data. The second appliance discoloration representation may be indicative of a second discoloration of the adhesive surface of the ostomy appliance, i.e. which part(s)/pixels of the appliance image data that are regarded or identified as the adhesive surface and have a second discoloration (e.g. second degree of output). The second appliance discoloration representation may be indicative of part(s)/pixels of the appliance image data having a color parameter, such as the red channel and/or the green channel of an RGB image, within a second range or larger than a second threshold. The second appliance discoloration representation may be indicative of part(s)/pixels of the adhesive surface with medium or high discoloration. Determining one or more ostomy representations may be based on the second appliance discoloration representation.

In one or more exemplary methods and/or devices, the one or more image representations comprises a stomal opening image representation, e.g. based on appliance image data and/or transformed appliance image data. The stomal opening image representation is indicative of the stomal opening, i.e. which part(s)/pixels of the appliance image data that are regarded or identified as the stomal opening. Determining one or more ostomy representations may be based on the stomal opening image representation. The stomal opening image representation may have a resolution of 256×256 pixels or more, such as 512×512 pixels.

The one or more image representations may comprise an appliance area representation, e.g. based on appliance image data and/or transformed appliance image data. The appliance area representation may be indicative of no appliance discoloration on the adhesive surface, i.e. no leak of output and thus which part(s)/pixels of the appliance image data that are regarded or identified as the adhesive surface and not being discoloured by output. Determining one or more ostomy representations may be based on the appliance area representation.

In one or more exemplary methods, determining one or more ostomy representations comprises determining an ostomy representation by combining a plurality of image representations. Determining one or more ostomy representations may comprise overlaying one or more image representations, such as one or more stoma discoloration representations, on the stoma image data or on the transformed stoma image data. Determining one or more ostomy representations may comprise overlaying one or more image representations, such as one or more appliance discoloration representations, on the appliance image data or on the transformed appliance image data.

Determining one or more ostomy representations, such as the first ostomy representation may comprise determining a discoloration map based on the stoma image data or on the transformed stoma image data and overlaying the discoloration map on the stoma image data or on the transformed stoma image data. In other words, the first ostomy representation may comprise a discoloration map.

Determining a discoloration map based on the stoma image data or on the transformed stoma image data may comprise assigning a first color value to pixels of the peristomal area that are discoloured to a first degree in a first range. Determining a discoloration map based on the stoma image data or on the transformed stoma image data may comprise assigning a second color value to pixels of the peristomal area that are discoloured to a second degree in a second range and/or assigning a third color value to pixels of the peristomal area that are discoloured to a third degree in a third range. Four, five, six, seven, nine, ten, or more different color values may be assigned to four, five, six, seven, nine, ten, or more different ranges. Thus, the discoloration map may comprise first pixels having a first color value, second pixels having a second color value and optionally third pixels having a third color value.

In one or more exemplary methods, determining one or more ostomy representations comprises determining a first ostomy representation and/or a second ostomy representation by combining a plurality of image representations.

The method comprises outputting one or more ostomy representations, e.g. the first ostomy representation and/or the second ostomy representation, and/or outputting the first ostomy parameter. Outputting first ostomy representation and/or first ostomy parameter may comprise displaying the first ostomy parameter or a first ostomy representation comprising the first ostomy parameter on a display of an accessory device. Outputting first ostomy representation and/or first ostomy parameter may comprise receiving, in the accessory device, the first ostomy representation and/or the first ostomy parameter. Outputting first ostomy representation and/or first ostomy parameter may comprise transmitting, with server device, the first ostomy representation and/or the first ostomy parameter, e.g. to the accessory device. Outputting ostomy representation(s) may comprise storing the ostomy representations in memory of the accessory device and/or server device.

Determining the one or more ostomy representations based on the image data may comprise determining a first ostomy representation, OR_1, based on the image data, ID, and/or transformed image data, ID_T, e.g. the stoma image data and/or the appliance image data. The first ostomy representation OR_1, also optionally denoted stoma representation, may be indicative of discoloration of the stomal area of the user. The first ostomy representation OR_1 may comprise or be overlaid on the stoma image data or transformed stoma image data. The first ostomy representation may comprise the first ostomy parameter, OP_1, and/or second ostomy parameter(s), P_2_1, P_2_2, . . . . The first ostomy representation may comprise stoma image data, SID, and/or transformed stoma image data, SID_T.

The method comprises determining one or more ostomy representations including a first ostomy parameter based on the one or more image representations.

The first ostomy parameter may be a discoloration index indicative of discoloration of the stomal area. The second ostomy parameter, also denoted OP_2, or second set of second ostomy parameters may be indicative of discoloration of the stomal area, such as indicative of discoloration severity percentage or degrees of discoloration of the peristomal area. The second set of ostomy parameters optionally comprises two or more second parameters, such as three, four, five, six, seven, eight, nine, ten or more second parameters. The second set of ostomy parameters optionally comprises a second primary ostomy parameter, also denoted OP_2_1, and a second secondary ostomy parameter, also denoted OP_2_2. The second set of ostomy parameters optionally comprises a second tertiary ostomy parameter, also denoted OP_2_3, and/or a second quaternary ostomy parameter, also denoted OP_2_4.

The first ostomy parameter may be indicative of how much of the peristomal area that is discoloured. For example, the first ostomy parameter OP_1 may be based on the one or more stoma discoloration representations and may be given by $$OP\_1 = N\_TOT/N\_PA,$$

Where N_TOT is the total number of discoloured pixels in the peristomal area and N_PA is the total number of pixels in the peristomal area.

The first ostomy parameter may be indicative of an area of discoloured peristomal area.

For example, the first ostomy parameter OP_1 may be based on the one or more stoma discoloration representations and may be given by $$OP\_1 = APP*N\_TOT$$

Where N_TOT is the total number of discoloured pixels in the peristomal area and APP is an area per pixel.

The area of a pixel APP may be given as:

$$AAP = HPP*WPP,$$

wherein HPP is the height per pixel and WPP is the width per pixel.

The height per pixel HPP may be based on one or more of the image representations, such as a stoma background image representation and/or an appliance background image representation.

The height per pixel, HPP may be given as:

$$HPP = AH/PH,$$

wherein AH is a height of the appliance (e.g. retrieved from a database) and PH is a pixel height of the appliance optionally determined as a number of pixels between two edges of the appliance counted along a vertical axis, e.g. in the appliance background image representation.

The width per pixel, WPP may be given as $$WPP = AW/PW,$$

wherein AW is a width of the appliance (e.g. retrieved from a database) and PW is a pixel width of the appliance optionally determined as the number of pixels between two edges of the appliance counted along a horizontal axis, e.g. in the appliance background image representation.

The method optionally comprises determining one or more second ostomy parameters based on the one or more image representations. The method optionally comprises outputting the one or more third second parameters.

A second primary ostomy parameter may be indicative of how many of the discoloured pixels in the peristomal area that are discoloured to a first degree or indicative of the area of pixels in the peristomal area that are discoloured to a first degree. For example, the second primary ostomy parameter OP_2_1 may be based on the one or more stoma discoloration representations and may be given by $$OP\_2\_1 = N\_DIS\_1/N\_TOT,$$

where N_DIS_1 is the number of discoloured pixels in the peristomal area that are discoloured to a first degree, e.g. less than 0.25, or to a first degree within a first range, where a discoloration of 0% corresponds to a first base color parameter indicative of a lower discoloration limit of the stoma and a discoloration of 100% corresponds to a second base color parameter indicative of a maximum red channel pixel value or a maximum combined channel pixel value in the second stoma image representation (stoma image representation indicative of the stoma). N_TOT is the total number of discoloured pixels in the peristomal area. In other words, the red channel pixel intensity of each pixel in the peristomal area is evaluated and compared to a discoloration scale where 0% corresponds to a minimum of discoloration of pixels in the fourth stoma image representation (a first discoloration representation indicative of a discoloration of the peristomal area) and where 100% corresponds to a maximum red channel pixel value in the second stoma image representation (stoma image representation indicative of the stoma). Put in another way, each pixel of the fourth stoma image representation is evaluated to assign a discoloration degree (selected from at least a first degree and a second degree) to each pixel of the in a plurality of discoloration degrees.

One or more second primary ostomy parameters may be indicative of the area, degree, or number of discoloured pixels within a first region of the peristomal area, such as within one or more first radial distances, e.g. 1 cm, 2 cm, and 3 cm, from the edge of the stoma. In other words, the first region may be seen as an inner area of the peristomal area.

One or more second secondary ostomy parameters may be indicative of the area, degree, or number of discoloured pixels within a second region of the peristomal area, such as outside one or more first radial distances, such as 1 cm, 2 cm, and 3 cm, from the edge of the stoma. In other words, the second region may be seen as an outer area of the peristomal area.

A second secondary ostomy parameter may be indicative of how many of the discoloured pixels in the peristomal area that are discoloured to a second degree or indicative of the area of pixels in the peristomal area that are discoloured to a second degree. For example, the second secondary ostomy parameter $OP\_2\_2$ may be based on the one or more stoma discoloration representations and may be given by $$OP\_2\_2 = N\_DIS\_2/N\_TOT,$$

where $N\_DIS\_2$ is the number of discoloured pixels in the peristomal area that are discoloured to a second degree, e.g. in a second range such as between 0.25 and 0.5, and $N\_TOT$ is the total number of discoloured pixels in the peristomal area.

A second tertiary ostomy parameter may be indicative of how many of the discoloured pixels in the peristomal area that are discoloured to a third degree or indicative of the area of pixels in the peristomal area that are discoloured to a third degree. For example, the second tertiary ostomy parameter $OP\_2\_3$ may be based on the one or more stoma discoloration representations and may be given by $$OP\_2\_3 = N\_DIS\_3/N\_TOT,$$

where $N\_DIS\_3$ is the number of discoloured pixels in the peristomal area that are discoloured to a third degree, e.g. in a third range such as between 0.5 and 0.75, and $N\_TOT$ is the total number of discoloured pixels in the peristomal area.

A second quaternary ostomy parameter may be indicative of how many of the discoloured pixels in the peristomal area that are discoloured to a fourth degree or indicative of the area of pixels in the peristomal area that are discoloured to a fourth degree. For example, the second quaternary ostomy parameter $OP\_2\_4$ may be based on the one or more stoma discoloration representations and may be given by $$OP\_2\_4 = N\_DIS\_4/N\_TOT,$$

where $N\_DIS\_4$ is the number of discoloured pixels in the peristomal area that are discoloured to a fourth degree, e.g. in a fourth range such as between 0.75 and 1 or larger than a threshold, and $N\_TOT$ is the total number of discoloured pixels in the peristomal area.

The first ostomy parameter may be a leakage parameter indicative of output distribution on the adhesive surface of the ostomy appliance. The second ostomy parameter or second set of second ostomy parameters may be leakage parameter(s) indicative of output distribution on the adhesive surface of the ostomy appliance.

The first ostomy parameter may be indicative of how much of the adhesive surface of the ostomy appliance that is discoloured. For example, the first ostomy parameter $OP\_1$ may be based on the one or more appliance discoloration representations and may be given by $$OP\_1 = N\_TOT/N\_AA,$$

Where $N\_TOT$ is the total number of discoloured pixels in the adhesive surface area and $N\_AA$ is the total number of pixels in the adhesive surface area.

The first ostomy parameter may be indicative of a discoloured area of the adhesive surface of the ostomy appliance. For example, the first ostomy parameter $OP\_1$ may be based on the one or more appliance discoloration representations and may be given by $$OP\_1 = APP * N\_TOT$$

Where $N\_TOT$ is the total number of discoloured pixels in the adhesive surface of the ostomy appliance and APP is an area per pixel.

The area of a pixel APP may be given as:

$$AAP = HPP * WPP,$$

wherein HPP is the height of a pixel and WPP is the width of a pixel.

The height of a pixel HPP may be based on one or more of the image representations, such as a stoma background image representation and/or an appliance background image representation.

The height of a pixel, HPP may be given as:

$$HPP = AH/PH,$$

wherein AH is a height of the appliance (e.g. retrieved from a database) and PH is a pixel height of the appliance optionally determined as a number of pixels between two edges of the appliance counted along a vertical axis, e.g. in the appliance background image representation.

The width per pixel, WPP may be given as $$WPP = AW/PW,$$

wherein AW is a width of the appliance (e.g. retrieved from a database) and PW is a pixel width of the appliance optionally determined as the number of pixels between two edges of the appliance counted along a horizontal axis, e.g. in the appliance background image representation.

The method may comprise determining one or more boundary lines based on the one or more image representations. The method may comprise determining a first boundary line, based on the one or more image representations, and wherein an ostomy representation comprises or is based on the first boundary line.

In one or more exemplary methods, the first boundary line may be indicative of a circumference or edge of a stomal area. The first boundary line may be indicative of a circumference or outer edge of an adhesive surface of the ostomy appliance.

The method may comprise determining a second boundary line, based on the one or more image representations, and wherein an ostomy representation comprises or is based on the second boundary line.

In one or more exemplary methods, the second boundary line may be indicative of a circumference or edge of the stoma. The second boundary line may be indicative of a circumference or inner edge of an adhesive surface of the ostomy appliance.

The method may comprise determining a third boundary line, based on the one or more image representations, and wherein an ostomy representation comprises or is based on the third boundary line.

In one or more exemplary methods, the third boundary line may be indicative of a boundary between a normal skin area of the peristomal area (non-discoloured) and a discoloured area of the peristomal area. The third boundary line may be indicative of a circumference or inner edge of an adhesive surface of the ostomy appliance.

The method may comprise determining a fourth boundary line e.g. based on the one or more image representations. Ostomy representation(s) and/or ostomy parameter(s), such as first and/or second ostomy parameter(s), may be based on the fourth boundary line. In one or more exemplary methods, the fourth boundary line may be indicative of a circumference of an output leakage on the adhesive surface of an ostomy appliance.

The first ostomy representation may comprise one or more boundary lines, such as the first boundary line and/or the second boundary line. The first ostomy representation may comprise the first ostomy parameter and/or one or more of the second ostomy parameters. The first ostomy representation may comprise the fourth boundary line.

Determining the one or more ostomy representations based on the image data may comprise determining a second ostomy representation based on the image data and/or transformed image data, e.g. the stoma image data and/or the appliance image data. The second ostomy representation, also denoted appliance representation, may be indicative of output distribution on the adhesive surface of the ostomy appliance. The second ostomy representation may comprise or be overlaid on the appliance image data or transformed appliance image data. The second ostomy representation may comprise one or more boundary lines, such as the first boundary line and/or the second boundary line. The second ostomy representation may comprise the third boundary line and/or the fourth boundary line.

Accordingly, determining one or more ostomy representations based on the image data may comprise determining boundary lines, e.g. of a first ostomy representation and/or of a second ostomy representation.

Determining one or more ostomy representations based on the image data may comprise determining a second ostomy parameter or a set of second ostomy parameters based on the image data and/or transformed image data, such as based on the stoma image data and/or the appliance image data.

The method optionally comprises determining one or more third ostomy parameters based on the one or more image representations. The method optionally comprises outputting the one or more third ostomy parameters.

A third primary ostomy parameter may be indicative of a shortest distance of a leakage of output to an edge of the ostomy appliance. The third ostomy parameter may be based on a first boundary line indicative of a circumference or outer edge of an adhesive surface of the ostomy appliance and a fourth boundary line indicative of a circumference of an output leakage on the adhesive surface of an ostomy appliance. The third ostomy parameter may be determined as a shortest (radial) distance between the first boundary line and the fourth boundary line. An angle may be associated with the third ostomy parameter, e.g. to indicate the direction in which the third ostomy parameter was measured or identified. The angle may be used for determining conversion parameter(s) for conversion between a pixel length and an absolute length.

In one or more exemplary methods, transforming the image data comprises determining a position parameter representative of a position of a camera image plane in relation to the stomal area and/or the adhesive surface, and wherein the transformed image data are based on the position parameter.

In one or more exemplary methods, the position parameter comprises an angle parameter representative of an angle between an optical axis of a camera being the source of the image data and an axial direction of the stomal area/normal to the adhesive surface. The transformed image data may be based on the angle parameter. In other words, transforming the image data may comprise determining an angle parameter representative of an angle between an optical axis of a camera being the source of the image data and an axial direction of the stomal area/normal to the adhesive surface. Thereby is enabled to compensate for image data that are not taken with the optical axis perpendicular to the adhesive surface of the ostomy appliance or perpendicular to the skin surface of the ostomist. Determining an angle parameter may comprise fitting the image data to a stomal area model image and/or an appliance model image and determining the angle parameter based on an image transformation providing a satisfactory fit of the image data to the stomal area model image and/or an appliance model.

In one or more exemplary methods, the position parameter comprises a distance parameter representative of a distance between a camera being the source of the image data and the stomal area/adhesive surface. The transformed image data may be based on the distance parameter. In other words, transforming the image data may comprise determining a distance parameter representative of a distance between a camera being the source of the image data and the stomal area/adhesive surface. A distance parameter allows for a (more precise) determination of a size of the stomal area/adhesive surface. Determining a distance parameter may comprise fitting the image data to a stomal area model image and/or an appliance model image and determining the distance parameter based on an image transformation providing a satisfactory fit of the image data to the stomal area model image and/or an appliance model.

In one or more exemplary methods, the position parameter comprises a rotation parameter representative of a rotational angle between an image axis of the image data and a reference axis of the stomal area/adhesive surface. The transformed image data may be based on the rotation parameter. The reference axis may be a vertical reference axis or a horizontal axis. In other words, transforming the image data may comprise determining a rotation parameter representative of a rotational angle between an image axis of the image data and a reference axis of the stomal area/adhesive surface. A rotation parameter allows to compensate for image data that are rotated, e.g. for a (more precise) determination of a directional ostomy condition. Determining a rotation parameter may comprise fitting the image data to a stomal area model image and/or an appliance model image and determining the rotation parameter based on an image transformation providing a satisfactory fit of the image data to the stomal area model image and/or an appliance model In one or more exemplary methods, transforming the image data comprises applying a geometric transformation to the image data. The geometric transformation may be based on the position parameter, e.g. one or more of angle parameter, distance parameter, and rotation parameter.

In one or more exemplary methods, transforming the image data comprises fitting the image data to a stomal area model image and/or an appliance model image. For example, transforming the image data may comprise fitting stoma image data to a stomal area model and/or fitting appliance image data to an appliance model image.

In one or more exemplary methods, transforming the image data comprises identifying a first stoma reference indicator on the stomal area. The transformed image data may be based on the first stoma reference indicator. The first stoma reference indicator may be a perimeter of the stoma or other parameters relating to the stoma, e.g. a center of the stoma. Transforming the image data may comprise identifying a second stoma reference indicator and/or a third stoma reference indicator on the stomal area. The transformed image data may be based on the second stoma reference indicator and/or the third stoma reference indicator, e.g. on and/or outside the stomal area. The second stoma reference indicator may be a scar or other body mark, such as a birthmark, belly button, etc. The third stoma reference indicator may be a scar or other body mark, such as a birthmark, belly button, etc. A stoma reference indicator may be indicative of a position and/or a direction of the stoma reference indicator.

In one or more exemplary methods, transforming the image data comprises identifying a first appliance reference indicator on the adhesive surface of the ostomy appliance. The transformed image data may be based on the first appliance reference indicator. The first appliance reference indicator may be a perimeter of the ostomy appliance (or a part thereof), a center of the stomal opening of the ostomy appliance, or a perimeter of the stomal opening of the ostomy appliance. An appliance reference indicator may be indicative of a position and/or a direction of the appliance reference indicator.

In one or more exemplary methods, transforming the image data comprises identifying a second appliance reference indicator on the adhesive surface of the ostomy appliance. The second appliance reference indicator may be different from the first appliance reference indicator and is optionally a perimeter of the ostomy appliance (or a part thereof), a center of the stomal opening of the ostomy appliance, or a perimeter or edge of the stomal opening of the ostomy appliance. The transformed image data may be based on the second appliance reference indicator.

In one or more exemplary methods, transforming the image data comprises scaling, such as downscaling, the image data to a predetermined pixel size, such as N×M pixels, where N may be in the range from 100 to 2,500, e.g. in the range from 100 to 1,000, such as 256 or 512, and where M may be in the range from 100 to 2,500, e.g. in the range from 100 to 1,000, such as 256 or 512. M may be different from N.

In one or more exemplary methods, transforming the image data comprises centering the image data about a center or center region of the image data. In one or more exemplary methods, transforming the image data comprises identifying and selecting a stoma region (stoma region data) of the image data and/or an appliance region (appliance region data) of the image data, and optionally transforming the stoma region and/or the appliance region for provision of respective transformed stoma image data and/or transformed appliance image data. Selecting a stoma region and/or an appliance region may comprise cutting out the stoma region and/or the appliance region from respective stoma image data and/or appliance image data. The stoma region comprises the stomal area, i.e. the stoma and the peristomal area.

In one or more exemplary methods, transforming the image data comprises identifying and selecting a stoma region, centering the stoma region, optionally rotating the stoma region (e.g. using a geometric transformation based on rotation parameter), and downscaling the rotated stoma region for provision of transformed stoma image data.

In one or more exemplary methods, transforming the image data comprises identifying and selecting an appliance region, centering the appliance region, optionally rotating the appliance region (e.g. using a geometric transformation based on rotation parameter), and downscaling the rotated appliance region for provision of transformed appliance image data.

In one or more exemplary methods, scaling the image data comprises determining a scaling parameter. The transformed image data may be based on the scaling parameter. In one or more exemplary methods, determining one or more ostomy representations may comprise upscaling a representation, such as a first representation and/or a second representation or parts thereof, based on the scaling parameter.

In one or more exemplary methods, transforming the image data comprises applying an image conversion to the image data, such as the stoma image data. The image conversion may be based on one or more color channels including the red channel R and optionally the blue channel and/or the green channel of the image being converted. The converted image I_C may be given as:

$$I\_C = \text{Abs}(R - \text{Average}(G-B)),$$

where R is the red channel in the image, G is the green channel, B is the blue channel. In other words, the red, blue, and green channels of the image may be converted into a single combined channel also denoted CC for each pixel of the image.

In one or more exemplary methods, obtaining image data comprises:
  detecting, with an accessory device, a user input indicative of a request for image capture;
  determining a position of the accessory device in relation to the adhesive surface of the ostomy appliance or in relation to the stomal area;
  determining if the position of the accessory device in relation to the adhesive surface of the ostomy appliance or in relation to the stomal area satisfies image capture criteria; and
  in accordance with a determination that the position of the accessory device in relation to the base plate of the ostomy appliance or in relation to the stomal area meets the image capture criteria,
    capturing image data of the ostomy appliance or the stomal area; and
    storing and/or transmitting the image data.

In one or more exemplary methods, obtaining image data comprises:
  in accordance with a determination that the position of the accessory device in relation to the adhesive surface of the ostomy appliance or in relation to stomal area does not meet the image capture criteria, providing feedback to the user, the feedback being indicative of erroneous position of the accessory device.

Providing feedback to the user may comprise displaying a user interface element on a display of the accessory device. Providing feedback to the user may comprise determining a property of the user interface element based on the position of the accessory device in relation to the adhesive surface of the ostomy appliance.

In one or more exemplary methods, the method comprises, after providing feedback to the user:
- determining a position of the accessory device in relation to the adhesive surface of the ostomy appliance;
- determining if the position of the accessory device in relation to the adhesive surface of the ostomy appliance satisfies image capture criteria; and
- in accordance with a determination that the position of the accessory device in relation to the adhesive surface of the ostomy appliance meets the image capture criteria, capturing image data of the ostomy appliance; and storing and/or transmitting the image data.

In one or more exemplary methods, determining a position of the accessory device in relation to the adhesive surface of the ostomy appliance comprises determining an angle between an optical axis of the camera and a proximal surface of the base plate.

In one or more exemplary methods, determining a position of the accessory device in relation to the stomal area comprises determining an angle between an optical axis of the camera and a reference surface of the stomal area, the reference surface being perpendicular to the axial direction.

In one or more exemplary methods, determining a position of the accessory device in relation to the adhesive surface of the ostomy appliance comprises determining a distance between the accessory device and the adhesive surface.

In one or more exemplary methods, the method comprises obtaining an ostomy appliance configuration, e.g. including an ostomy appliance identifier, and wherein determining a position of the accessory device in relation to the adhesive surface of the ostomy appliance is based on the ostomy appliance configuration.

FIG. 1 shows a flow chart of an exemplary method for classifying an ostomy condition. The method 100 comprises obtaining 2 image data, e.g. with an accessory device. The image data, ID, comprises stoma image data, SID, of a stomal area including a stoma and/or appliance image data, AID, of an adhesive surface of an ostomy appliance. Thus, the method 100 optionally comprises obtaining 102A stoma image data and/or obtaining 102B appliance image data. The method 100 comprises determining S104 one or more ostomy representations, such as a first ostomy representation, including a first ostomy parameter based on the image data, e.g. based on SID and/or AID; and optionally outputting S106 the first ostomy parameter. The method 100 optionally comprises transforming S108 the image data, and determining S104 the one or more ostomy representations based on the image data comprises determining S104A the first ostomy parameter based on the transformed image data (transformed appliance image data AID_T and/or transformed stoma image data SID_T).

Determining S104 one or more ostomy representations optionally comprises determining S104B one or more image representations based on the image data or transformed image data; and determining S104C one or more ostomy representations including a first ostomy parameter based on the one or more image representations.

Determining S104B one or more image representations based on the image data or transformed image data optionally comprises determining S104BA one or more stoma image representations indicative of the stomal area and optionally determining S104BB one or more appliance image representations indicative of the adhesive surface of the ostomy appliance.

In one or more exemplary methods, the one or more stoma image representations comprises at least four stoma image representations including a first stoma image representation SIR_1, a second stoma image representation SIR_2, a third stoma image representation SIR_3, and a fourth stoma image representation SIR_4.

The first stoma image representation may be a stoma background image representation indicative of a background of the stoma image data, i.e. which part(s)/pixels of the stoma image data that are regarded or identified as background, i.e. outside the area covered by the adhesive surface (e.g. including part of user skin not covered by adhesive surface of ostomy appliance).

The second stoma image representation may be a stoma image representation indicative of the stoma, i.e. which part(s)/pixels of the ostomy image data that are regarded or identified as the stoma.

The third stoma image representation may be a normal skin image representation indicative of the normal skin of the peristomal area, i.e. which part(s)/pixels of the ostomy image data that are regarded or identified as not having discoloration.

The fourth stoma image representation may be a first discoloration representation indicative of a discoloration of the peristomal area, i.e. which part(s)/pixels of the ostomy image data that are regarded or identified as the peristomal area and discoloured.

In one or more exemplary methods, the one or more appliance image representations comprises at least three or at least four appliance image representations including a first appliance image representation AIR_1, optionally a second appliance image representation AIR_2, a third appliance image representation AIR_3, and a fourth appliance image representation AIR_4.

The first appliance image representation may be an appliance background image representation indicative of a background of the appliance image data, i.e. which part(s)/pixels of the appliance image data/transformed appliance image data that are regarded or identified as background (e.g. image part(s)/pixel(s) outside the area of the adhesive surface of the ostomy appliance).

The second appliance image representation may be a stomal opening image representation indicative of the stomal opening, i.e. which part(s)/pixels of the appliance image data/transformed appliance image data that are regarded or identified as the stomal opening.

The third appliance image representation may be an appliance area representation indicative of no appliance discoloration on the adhesive surface, i.e. no leak of output and thus which part(s)/pixels of the appliance image data/transformed appliance image data that are regarded or identified as the adhesive surface and not being discoloured by output.

The fourth appliance image representation may be a first appliance discoloration representation indicative of a discoloration of the adhesive surface of the ostomy appliance, i.e. which part(s)/pixels of the appliance image data that are regarded or identified as the adhesive surface and have a discoloration (leak of output).

Determining S104C one or more ostomy representations including a first ostomy parameter based on the one or more image representations optionally comprises determining S104CA a first ostomy representation OR_1 comprising the first ostomy parameter OP_1 based on one or more stoma image representations.

In one or more exemplary methods, the first ostomy representation OR_1 may be based on the first stoma image representation SIR_1, the second stoma image representation SIR_2, the third stoma image representation SIR_3, and the fourth stoma image representation SIR_4. The first ostomy representation OR_1 may comprise or be based on the ostomy image data/transformed ostomy image data.

Determining S104CA the first ostomy representation optionally comprises determining a second ostomy parameter OP_2 or a set of second ostomy parameters. In other words, the first ostomy representation OR_1 may comprise OP_1, and one or more second ostomy parameters.

Determining S104C one or more ostomy representations including a first ostomy parameter based on the one or more image representations optionally comprises determining S104CB a second ostomy representation OR_2 based on one or more appliance image representations.

In one or more exemplary methods, the second ostomy representation OR_2 may be based on the first appliance image representation, optionally the second appliance image representation, the third appliance image representation, and the fourth appliance image representation.

Outputting S106 the first ostomy parameter may comprise storing S106A the first ostomy parameter or a first ostomy representation comprising the first ostomy parameter in a memory and/or transmitting S106B the first ostomy parameter or a first ostomy representation comprising the first ostomy parameter to an accessory device and/or server device. Outputting S106 the first ostomy parameter may comprise displaying S106C the first ostomy parameter or a first ostomy representation comprising the first ostomy parameter on a display of an accessory device. Thereby a user and/or professional caretaker is able to verify and act on an ostomy condition in substantially real-time. For example, a user is able to or can be prompted to take measures to reduce the effects of an ostomy condition when changing the ostomy appliance, e.g. during a changing procedure in substantially real-time.

The method 100 comprises outputting 110 one or more ostomy representations, e.g. including the first ostomy representation OR_1 and/or the second ostomy representation OR_2. Outputting 110 one of more ostomy representations may comprise outputting 112 a second ostomy representation. Outputting S112 the second ostomy representation may comprise storing S112A the second ostomy representation in a memory and/or transmitting S112B the second ostomy representation to an accessory device and/or server device. Outputting S112 the second ostomy representation may comprise displaying S112C the second ostomy representation on a display of an accessory device. Thereby a user and/or professional caretaker is able to verify and act on an ostomy condition in substantially real-time. For example, a user is able to or can be prompted to take measures to reduce the effects of an ostomy condition when changing the ostomy appliance, e.g. during a changing procedure in substantially real-time.

Transforming S108 the image data comprises determining S108A a position parameter representative of a position of a camera image plane in relation to the stomal area and/or the adhesive surface, and wherein the transformed image data are based on the position parameter.

The position parameter optionally comprises an angle parameter representative of an angle between an optical axis of a camera being the source of the image data and an axial direction of the stomal area/normal to the adhesive surface and wherein the transformed image data are based on the angle parameter. Thus, determining S108A a position parameter may comprise determining 108B an angle parameter representative of an angle between an optical axis of a camera being the source of the image data and an axial direction of the stomal area/normal to the adhesive surface, and wherein the transformed image data are based on the angle parameter.

The position parameter optionally comprises a distance parameter representative of a distance between a camera being the source of the image data and the stomal area/adhesive surface, and wherein the transformed image data are based on the distance parameter. Thus, determining S108A a position parameter may comprise determining 108C a distance parameter representative of a distance between a camera being the source of the image data and the stomal area/adhesive surface, and wherein the transformed image data are based on the distance parameter.

The position parameter optionally comprises a rotation parameter representative of a rotational angle between an image axis of the image data and a reference axis of the stomal area/adhesive surface. Thus, determining S108A a position parameter may comprise determining 108D a rotation parameter representative of a rotational angle between an image axis of the image data and a reference axis of the stomal area/adhesive surface, and wherein the transformed image data are based on the rotation parameter.

In method 100, transforming S108 the image data optionally comprises identifying S108E one or more reference indicators of the image data, e.g. a first stoma reference indicator and/or a second stoma reference indicator of the stoma image data and/or a first appliance reference indicator and/or a second appliance reference indicator of the appliance image data. The transformed image data are optionally based on the reference indicator(s).

In method 100, transforming S108 the image data optionally comprises scaling S108F the image data to a predetermined pixel size, e.g. to a pixel size of 256×256 pixels. Scaling the image data comprises determining a scaling parameter, and wherein the transformed image data are based on the scaling parameter.

In method 100, transforming S108 the image data optionally comprises centering 108G the image data about a center or center region of the image data, e.g. based on a reference indicator (position and/or direction) of respective stoma image data and/or appliance image data. For example, transforming stoma image data may comprise centering the stoma image data about a center, perimeter, or center region of the stoma (e.g. identified as a first or second stoma reference identifier in S108E). In one or more exemplary methods, transforming appliance image data may comprise centering the appliance image data about a center, perimeter, or center region of the stomal opening of the ostomy appliance/baseplate and/or about a perimeter of the adhesive surface/baseplate of the ostomy appliance (e.g. identified as a first or second appliance reference identifier in S108E).

Figure 2:
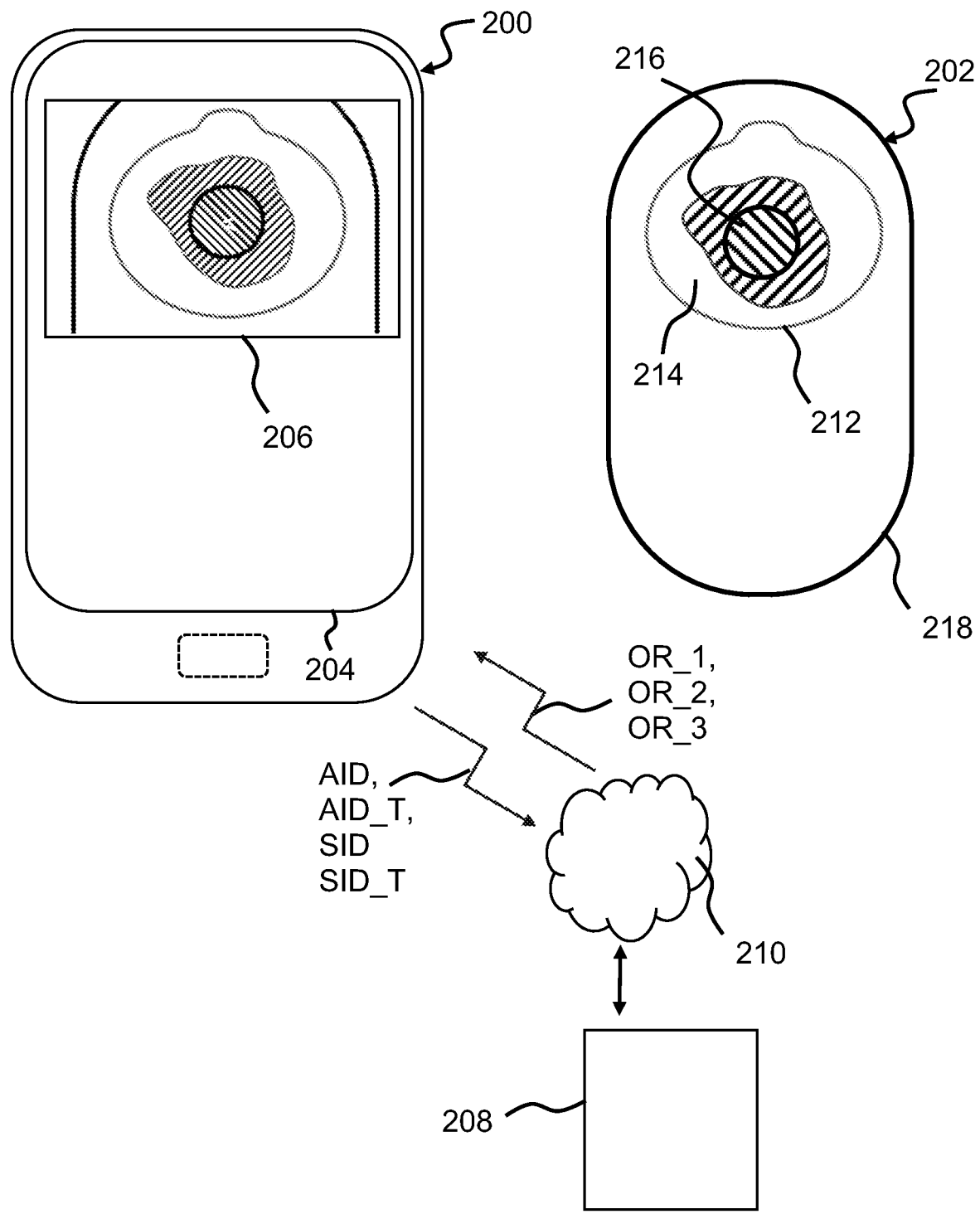
FIG. 2 illustrates an ostomy appliance and an accessory device

FIG. 2 shows an accessory device 200 and an ostomy appliance 202. The accessory device 200 is embodied as a smartphone and comprises a display 204 displaying an appliance image 206 representing appliance image data obtained by a camera of the accessory device 200. The accessory device 200 transmits the appliance image data AID and/or transformed appliance image data AID_T to server device 208 via network 210. The server device 210 determines one or more ostomy representations including one or more of first ostomy representation OR_1, second ostomy representation OR_2, and third ostomy representation OR_3, and outputs ostomy representation(s) by transmitting ostomy representation(s) to the accessory device 200. The accessory device 200 determines ostomy representation(s) by receiving, with the accessory device 200, the one or more ostomy representations from server device 208 and outputs ostomy representation(s) by displaying the first ostomy parameter or a first ostomy representation comprising the first ostomy parameter on the display 204 (not shown in FIG. 2). The ostomy appliance 202 comprises a baseplate 212 with adhesive surface 214 and stomal opening 216. An ostomy bag 218 is attached to the baseplate 212 for collection of output. During use, output 220 may leak between the adhesive surface and the skin surface of the user. Such output leakage may irritate and damage the skin due to the highly aggressive behaviour of the output. The present disclosure provides fast, uniform and reliable analysis and communication of such a leakage or ostomy condition based on the appliance image data.

Figure 3:
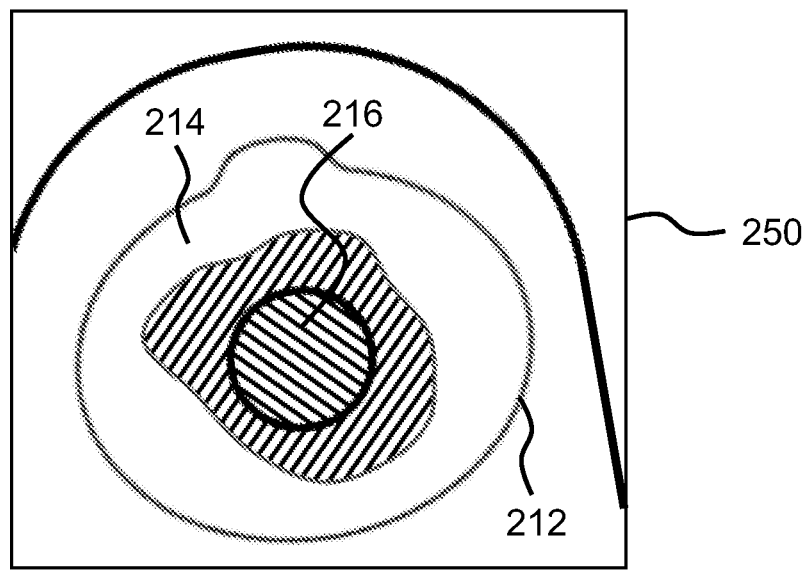
FIG. 3 is an appliance image of appliance image data

FIG. 3 shows an appliance image 250 (of ostomy appliance 202) representative of exemplary appliance image data captured with a camera of the accessory device 200. As can be seen, the user taking the appliance image 250 have rotated the camera slightly counter-clockwards and have not been able to center the stomal opening of the ostomy appliance.

Figure 4:
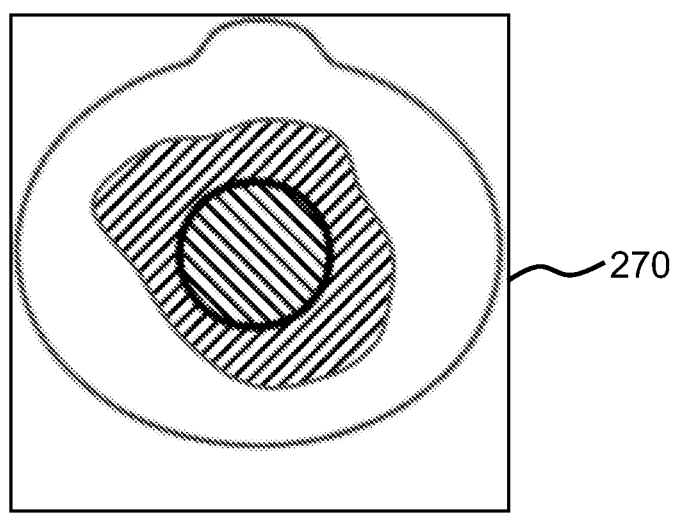
FIG. 4 is an appliance image of transformed appliance image data
Figure 5:
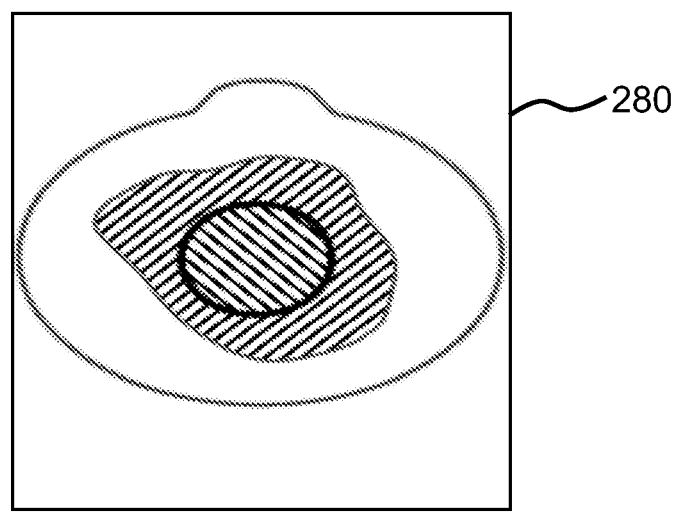
FIG. 5 is an appliance image of appliance image data

FIG. 4 shows an appliance image 270 representative of exemplary transformed appliance image data based on the appliance image data of FIG. 3 or FIG. 5. The appliance image data of appliance image 250 have been centered, rotated, e.g. by using geometric transformation, and downscaled to 256×256 pixels to provide transformed appliance data of appliance image 270.

FIG. 5 shows an appliance image 280 (of ostomy appliance 202) representative of exemplary appliance image data captured with a camera of the accessory device 200. As can be seen, the user taking the appliance image 280 have tilted the camera slightly such that the optical axis of the camera and a normal to the adhesive surface are slightly angled/not parallel. In this case, the appliance image data of appliance image 280 have been transformed by applying a geometric transformation based on an angle parameter, and downscaled to 256×256 pixels to provide transformed appliance data of image 270.

Figure 6:
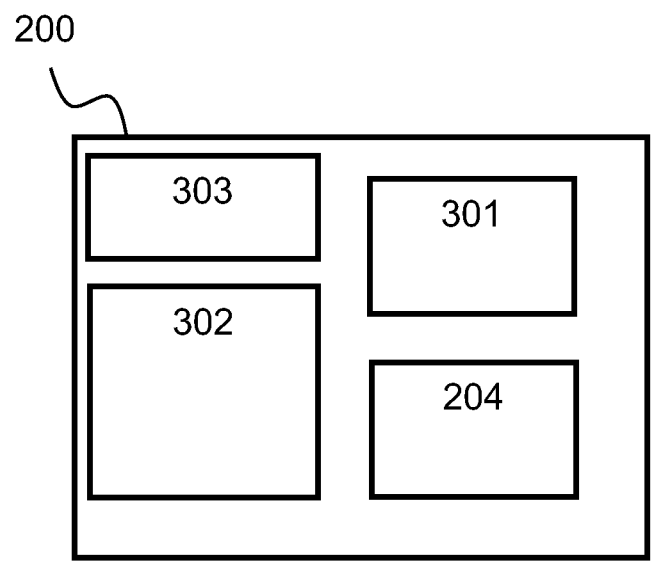
FIG. 6 is a block diagram of an exemplary accessory device

FIG. 6 is a block diagram illustrating an exemplary accessory device 200 according to this disclosure. The present disclosure relates to an accessory device 200 of an ostomy system. The accessory device comprises a display 204, memory module 301, a processor module 302, and a wireless interface 303. The accessory device 200 is configured to perform any of the methods disclosed herein, such as any of the methods shown in FIG. 1. The processor module 302 may be configured to perform any or at least some of the steps S102, S102A, S102B, S104, S104A, S104B, S104BA, S104BB, S104C, S104CA, S104CB, S104CC, S106, S106A, S106B, S106C, S108, S108A, S108B, S108C, S108D, S108E, S108F, S108G, S110, S112, S112A, S112B, S112C, see FIG. 1 and related description.

The operations of the accessory device 200 may be embodied in the form of executable logic routines (e.g., lines of code, software programs, etc.) that are stored on a non-transitory computer readable medium (e.g., the memory module 301) and are executed by the processor module 302. Furthermore, the operations of the accessory device 200 may be considered a method that the accessory device 200 is configured to carry out. Also, while the described functions and operations may be implemented in software, such functionality may as well be carried out via dedicated hardware or firmware, or some combination of hardware, firmware and/or software.

The memory module 301 may be one or more of a buffer, a flash memory, a hard drive, a removable media, a volatile memory, a non-volatile memory, a random access memory (RAM), or other suitable device. In a typical arrangement, the memory module 301 may include a non-volatile memory for long term data storage and a volatile memory that functions as system memory for the processor module 302. The memory module 301 may exchange data with the processor module 302 over a data bus. Control lines and an address bus between the memory module 301 and the processor module 302 also may be present (not shown in FIG. 6). The memory module 301 is considered a non-transitory computer readable medium.

Figure 7:
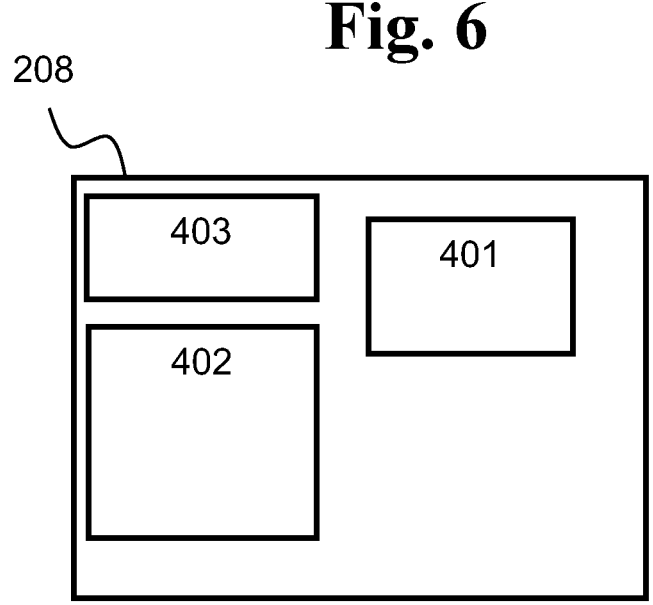
FIG. 7 is a block diagram of an exemplary server device

FIG. 7 is a block diagram illustrating an exemplary server device 208 according to this disclosure. The present disclosure relates to a server device 208 of an ostomy system. The server device comprises a memory module 401, a processor module 402, and an interface 403. The server device 208 is configured to perform any of the methods disclosed herein, such as any of the methods shown in FIG. 1. The processor module 402 may be configured to perform any or at least some of the steps S102, S102A, S102B, S104, S104A, S104B, S104BA, S104BB, S104C, S104CA, S104CB, S104CC, S106, S106A, S106B, S106C, S108, S108A, S108B, S108C, S108D, S108E, S108F, S108G, S110, S112, S112A, S112B, S112C, see FIG. 1 and related description.

The operations of the server device 208 may be embodied in the form of executable logic routines (e.g., lines of code, software programs, etc.) that are stored on a non-transitory computer readable medium (e.g., the memory module 401) and are executed by the processor module 402. Furthermore, the operations of the server device 208 may be considered a method that the server device 208 is configured to carry out. Also, while the described functions and operations may be implemented in software, such functionality may as well be carried out via dedicated hardware or firmware, or some combination of hardware, firmware and/or software.

The memory module 401 may be one or more of a buffer, a flash memory, a hard drive, a removable media, a volatile memory, a non-volatile memory, a random access memory (RAM), or other suitable device. In a typical arrangement, the memory module 401 may include a non-volatile memory for long term data storage and a volatile memory that functions as system memory for the processor module 402. The memory module 401 may exchange data with the processor module 402 over a data bus. Control lines and an address bus between the memory module 401 and the processor module 402 also may be present (not shown in FIG. 7). The memory module 401 is considered a non-transitory computer readable medium.

Figure 8:
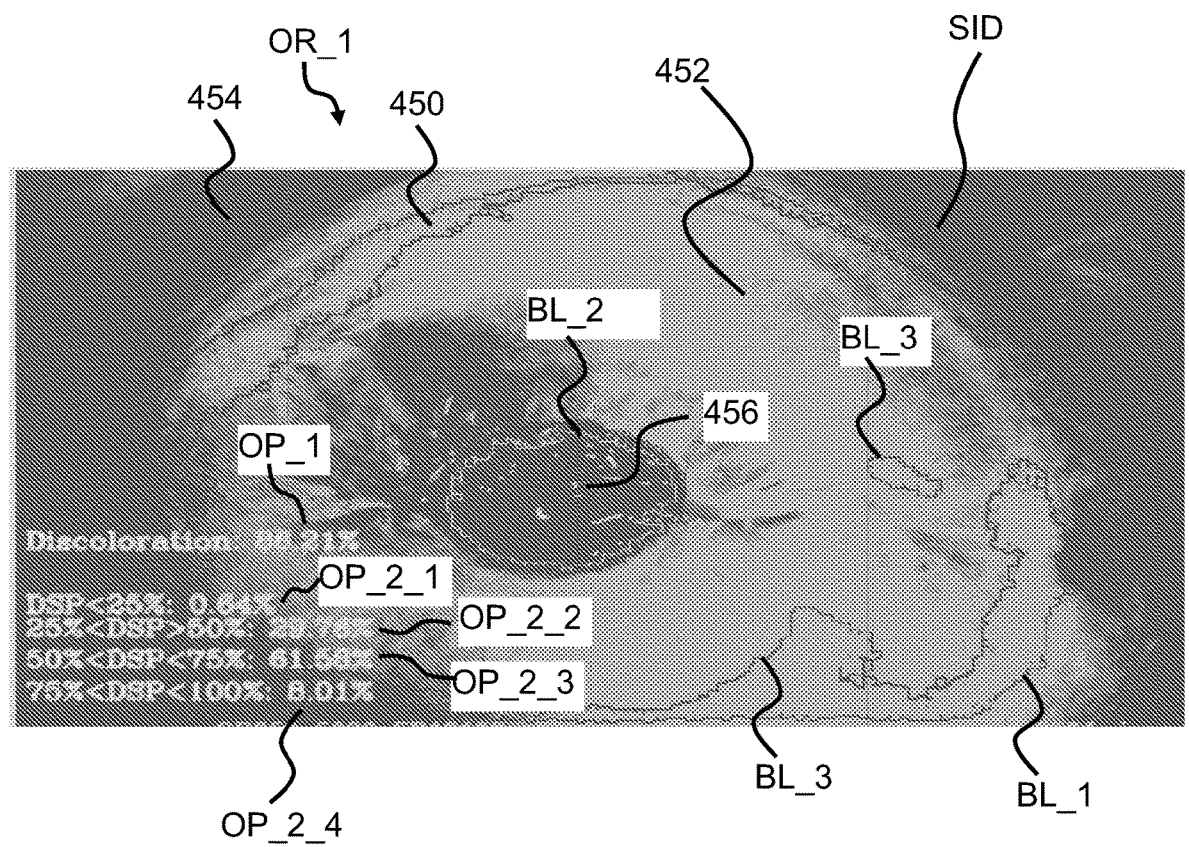
FIG. 8 shows an exemplary first ostomy representation

FIG. 8 illustrates an exemplary first ostomy representation OR_1. The first ostomy representation OR_1 comprises a first ostomy parameter OP_1 indicative of the indicative of discoloration of the stomal area (OP_1=86.21% in the illustrated example). The first ostomy representation OR_1 comprises second ostomy parameters OP_2_1, OP_2_2, OP_2_3, and OP_2_4 indicative of discoloration severity percentage. The second primary ostomy parameter OP_2_1 (OP_2_1=0.64%) is indicative of the number of discoloured pixels with a first degree (DSP<25%) of discoloration out of the number of discoloured pixels. The second secondary ostomy parameter OP_2_2 (OP_2_2=29.76%) is indicative of the number of discoloured pixels with a second degree (25%<DSP<50%) of discoloration out of the number of discoloured pixels. The second tertiary ostomy parameter OP_2_3 (OP_2_1=61.58%) is indicative of the number of discoloured pixels with a third degree (50%<DSP<75%) of discoloration out of the number of discoloured pixels. The second quaternary ostomy parameter OP_2_4 (OP_2_4=8.01%) is indicative of the number of discoloured pixels with a fourth degree (75%<DSP<100%) of discoloration out of the number of discoloured pixels. The set of second ostomy parameters is determined based on the fourth stoma image representation.

The first ostomy representation OR_1 comprises first boundary line BL_1 (red line) indicative of a circumference or edge of the stomal area, e.g. indicative of a boundary between the normal skin area 450 and background 454 of the stoma image data. The first boundary line is based on the first stoma image representation and/or the third stoma image representation.

The first ostomy representation OR_1 comprises second boundary line BL_2 (green line) indicative of a circumference or edge of the stoma 456, wherein the second boundary line is based on the second stoma image representation and/or the fourth stoma image representation.

The first ostomy representation OR_1 comprises third boundary lines BL_3 (blue lines) indicative of a boundary between a normal skin area 450 of the peristomal area (non-discoloured) and a discoloured area 452 of the peristomal area. The third boundary lines BL_3 are based on the third stoma image representation and/or the fourth stoma image representation.

The first ostomy representation OR_1 comprises or is overlaid on the stoma image data SID on which the first ostomy representation OP_1 is based.

Figure 9:
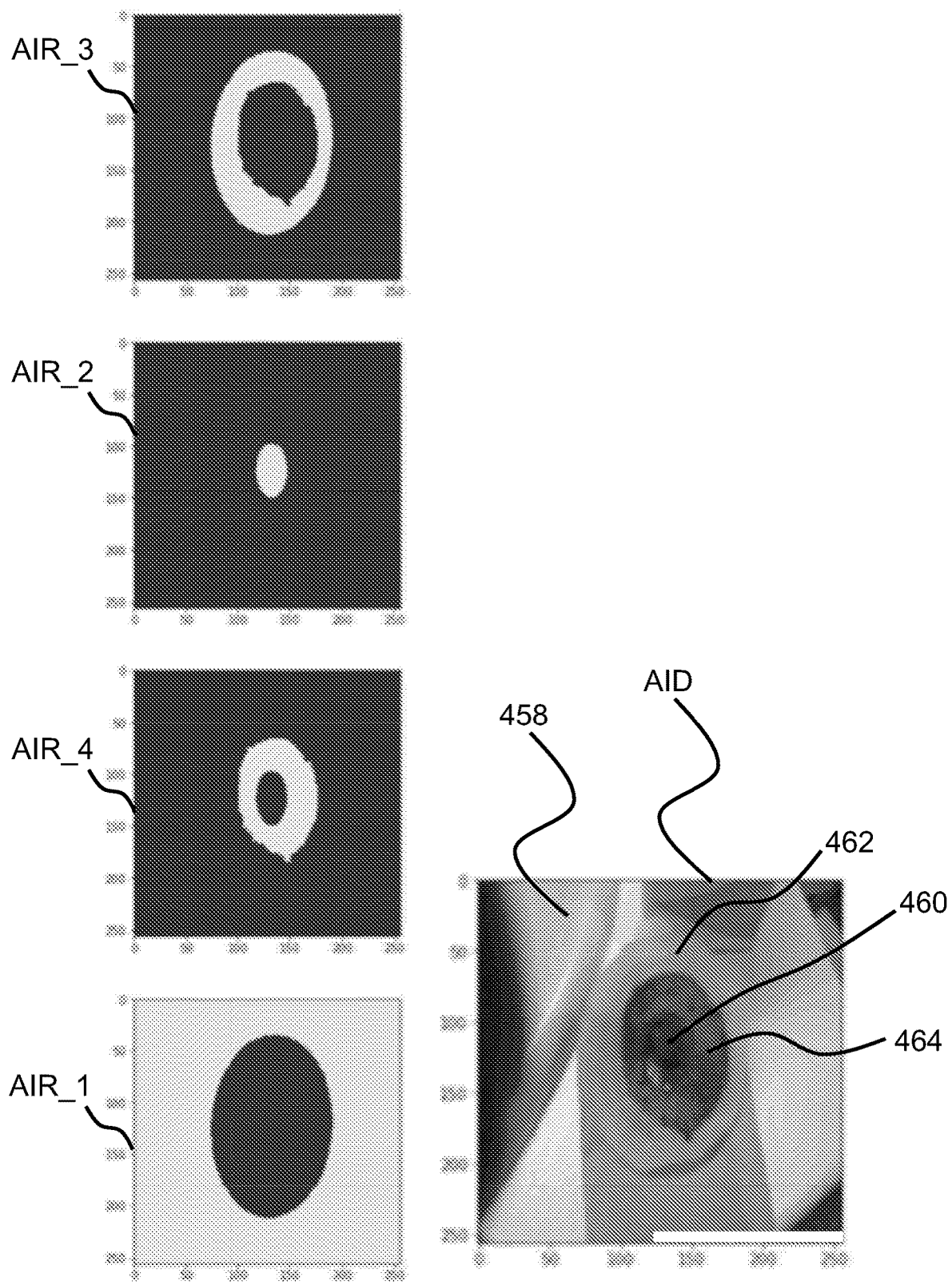
FIG. 9 shows exemplary appliance image representations

FIG. 9 shows exemplary appliance image representations with appliance image data AID forming the basis therefore. The first appliance image representation AIR_1 of 256×256 pixels being an appliance background image representation (binary mask) indicative of a background 458 of the appliance image data, i.e. which part(s)/pixels of the appliance image data/transformed appliance image data that are regarded or identified as background (e.g. image part(s)/pixel(s) outside the area of the adhesive surface of the ostomy appliance). Yellow represents the binary value 1 of the binary mask (i.e. pixel is part of background) and purple represents the binary value 0 (i.e. pixel is not part of background).

The second appliance image representation AIR_2 of 256×256 pixels is a stomal opening image representation indicative of the stomal opening 460, i.e. which part(s)/pixels of the appliance image data/transformed appliance image data that are regarded or identified as the stomal opening. Yellow represents the binary value 1 of the binary mask (i.e. pixel is part of stomal opening) and purple represents the binary value 0 (i.e. pixel is not part of stomal opening).

The third appliance image representation AIR_3 of 256×256 pixels is an appliance area representation indicative of no appliance discoloration (clean adhesive surface 462) on the adhesive surface of the ostomy appliance, i.e. no leak of output and thus which part(s)/pixels of the appliance image data/transformed appliance image data that are regarded or identified as the adhesive surface and not being discoloured by output. Yellow represents the binary value 1 of the binary mask (i.e. pixel is not discoloured) and purple represents the binary value 0 (i.e. pixel is not part of non-discoloured adhesive surface).

The fourth appliance image representation AIR_4 of 256×256 pixels is a first appliance discoloration representation indicative of a discoloration (discoloured adhesive surface 464) of the adhesive surface of the ostomy appliance, i.e. which part(s)/pixels of the appliance image data that are regarded or identified as the adhesive surface and have a discoloration (leak of output). Yellow represents the binary value 1 of the binary mask (i.e. pixel is discoloured) and purple represents the binary value 0 (i.e. pixel is not part of discoloured adhesive surface).

Figure 10:
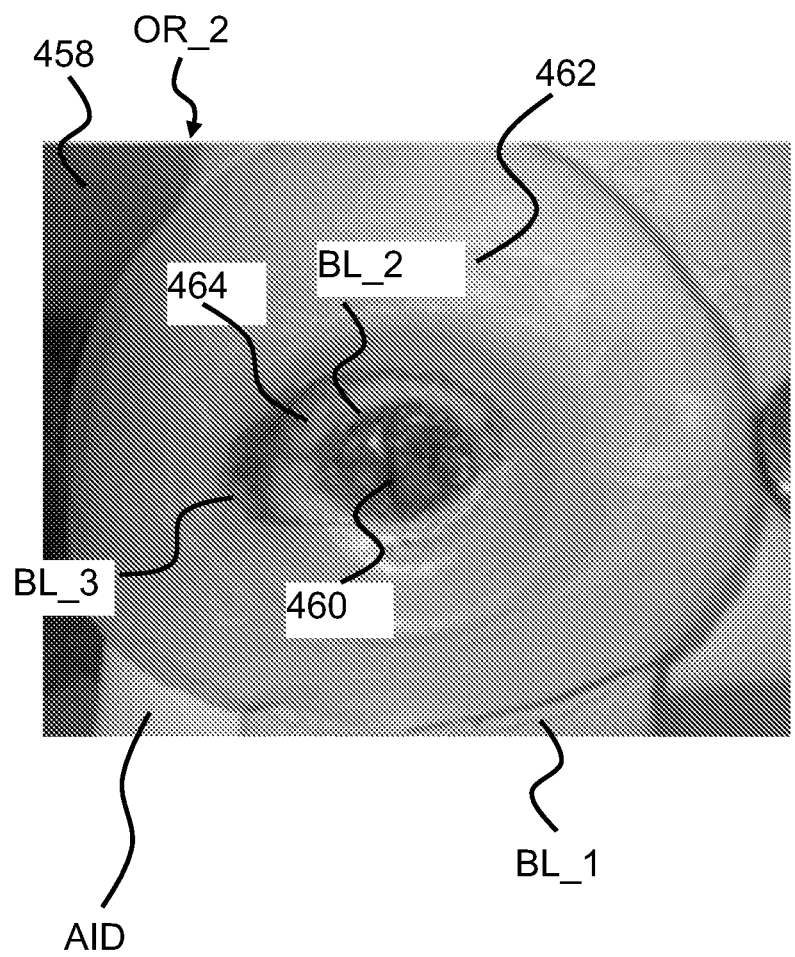
FIG. 10 shows an exemplary second ostomy representation

FIG. 10 shows an exemplary second ostomy representation OR_2 based on four appliance image representations as also described in relation to FIG. 9. The second ostomy representation OR_2 comprises a first boundary line BL_1 (red line) indicative of a circumference or edge of the adhesive surface of the ostomy appliance. The first boundary line BL_1 is based on the first appliance image representation and/or the third appliance image representation.

The second ostomy representation OR_2 comprises second boundary line BL_2 (green line) indicative of a circumference or edge of the stomal opening of the adhesive surface, wherein the second boundary line is based on the second appliance image representation and/or the fourth appliance image representation.

The second ostomy representation OR_2 comprises third boundary line BL_3 (blue line) indicative of a boundary between a discoloured part (output leak) and a non-discoloured part (clean) of the adhesive surface. The third boundary lines BL_3 are based on the third stoma image representation and/or the fourth stoma image representation.

The second ostomy representation OR_2 comprises or is overlaid on the appliance image data AID on which the second ostomy representation OP_2 is based.

Figure 11:
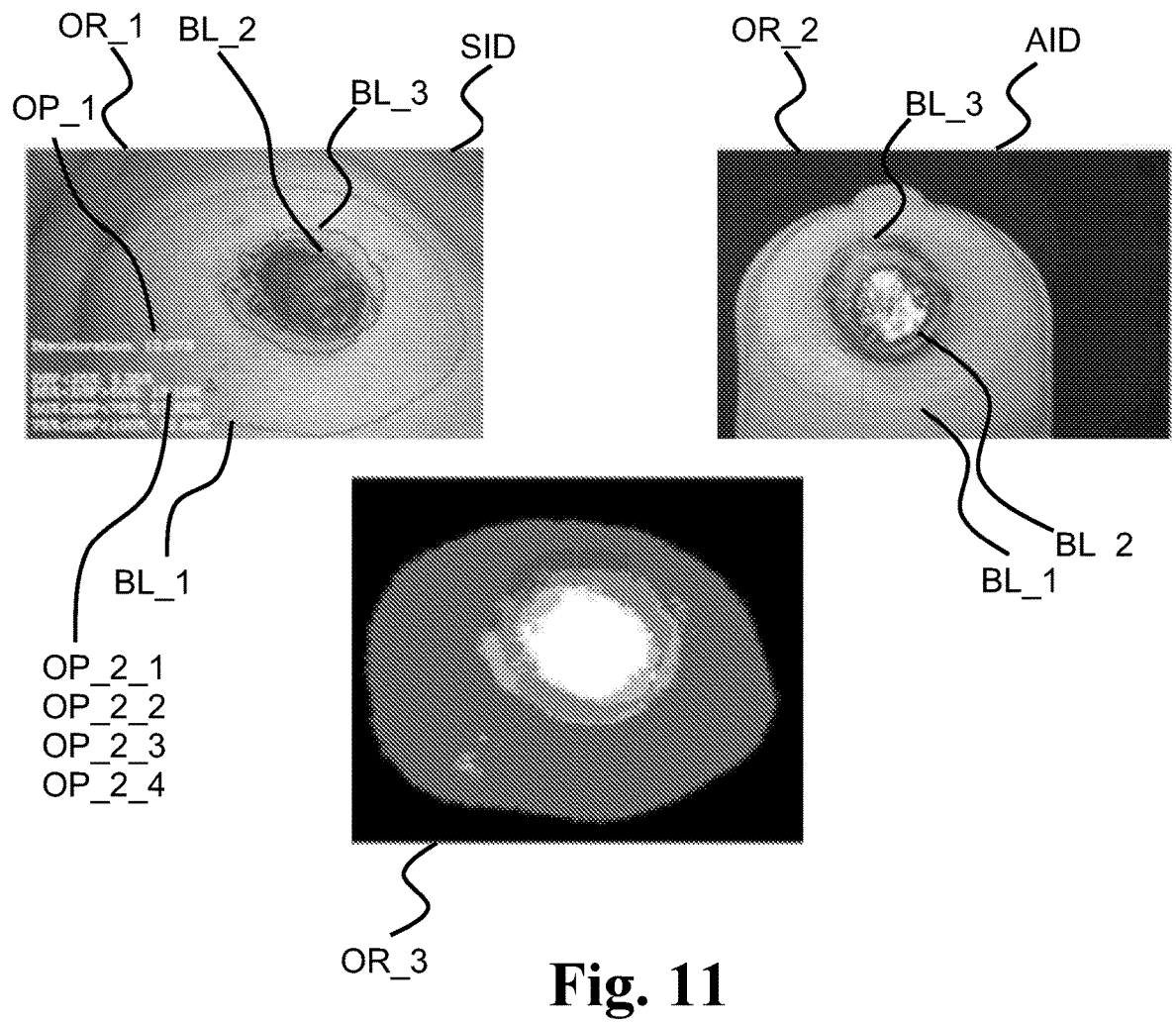
FIG. 11 shows exemplary ostomy representations

FIG. 11 shows exemplary ostomy representations OR_1, OR_2, and OR_3 for corresponding stoma image data SID and appliance image data AID. The third ostomy representation OR_3 is based on one or more of the stoma image representations and one or more appliance image representations. In the third ostomy representation, the blue part is indicative of the fourth appliance image representation and the light gray part is indicative of the discoloured part of the peristomal area, i.e. indicative of the third stoma image representation.

Also disclosed are methods according to any of the following items.

Item 1. Methods for classifying an ostomy condition, the method comprising:
  obtaining image data, the image data comprising stoma image data of a stomal area including a stoma and/or appliance image data of an adhesive surface of an ostomy appliance;
  determining one or more ostomy representations including a first ostomy parameter based on the image data; and
  outputting the first ostomy parameter,
wherein the method comprises transforming the image data, and wherein determining the one or more ostomy representations based on the image data comprises determining the first ostomy parameter based on the transformed image data.

Item 2. Method according to item 1, wherein transforming the image data comprises determining a position parameter representative of a position of a camera image plane in relation to the stomal area and/or the adhesive surface, and wherein the transformed image data are based on the position parameter.

Item 3. Method according to item 2, wherein the position parameter comprises an angle parameter representative of an angle between an optical axis of a camera being the source of the image data and an axial direction of the stomal area/normal to the adhesive surface and wherein the transformed image data are based on the angle parameter.

Item 4. Method according to any of items 2-3, wherein the position parameter comprises a distance parameter representative of a distance between a camera being the source of the image data and the stomal area/adhesive surface, and wherein the transformed image data are based on the distance parameter.

Item 5. Method according to any of items 2-4, wherein the position parameter comprises a rotation parameter representative of a rotational angle between an image axis of the image data and a reference axis of the stomal area/adhesive surface, and wherein the transformed image data are based on the rotation parameter.

Item 6. Method according to any of items 1-5, wherein transforming the image data comprises fitting the image data to a stomal area model image and/or an appliance model image.

Item 7. Method according to any of items 1-6, wherein transforming the image data comprises identifying a first stoma reference indicator on the stomal area, and wherein the transformed image data are based on the first stoma reference indicator.

Item 8. Method according to item 7, wherein the first stoma reference indicator is a perimeter of the stoma.

Item 9. Method according to any of items 1-8, wherein transforming the image data comprises identifying a first appliance reference indicator on the adhesive surface of the ostomy appliance, and wherein the transformed image data are based on the first appliance reference indicator.

Item 10. Method according to item 9, wherein the first appliance reference indicator is a perimeter of the ostomy appliance.

Item 11. Method according to any of items 1-10, wherein transforming the image data comprises identifying a second appliance reference indicator on the adhesive surface of the ostomy appliance, wherein the transformed image data are based on the second appliance reference indicator, and wherein the second appliance reference indicator is an edge of a stomal opening of the ostomy appliance.

Item 12. Method according to any of items 1-11, wherein transforming the image data comprises scaling the image data to a predetermined pixel size.

Item 13. Method according to item 12, wherein scaling the image data comprises determining a scaling parameter, and wherein the transformed image data are based on the scaling parameter.

Item 14. Method according to any of items 1-13, wherein the first ostomy parameter is a discoloration index indicative of discoloration of the stomal area.

Item 15. Method according to any of items 1-14, wherein the first ostomy parameter is a leakage parameter indicative of output distribution on the adhesive surface.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It may be appreciated that FIGS. 1-7 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES

100 method for classifying an ostomy condition
S102 obtaining image data
S102A obtaining stoma image data
S102B obtaining appliance image data
S104 determining one or more ostomy representations
S104A determining the first ostomy parameter based on the transformed image data
S104B determining one or more image representations
S104BA determining one or more stoma image representations
S104BB determining one or more appliance image representations S104C determining one or more ostomy representations including a first ostomy parameter based on the one or more image representations
S104CA determining a first ostomy representation
S104CB determining a second ostomy representation
S104CC determining a third ostomy representation
S106 outputting first ostomy representation/first ostomy parameter
S106A storing the first ostomy parameter or a first ostomy representation comprising the first ostomy parameter
S106B transmitting with server device and/or receiving with accessory device the first ostomy parameter or a first ostomy representation comprising the first ostomy parameter
S106C displaying the first ostomy parameter or a first ostomy representation comprising the first ostomy parameter
S108 transforming the image data
S108A determining a position parameter
S108B determining an angle parameter
S108C determining a distance parameter
S108D determining a rotation parameter
S108E identifying one or more reference indicators of the image data
S108F scaling the image data to a predetermined pixel size
S108G centering the image data
S110 outputting one or more ostomy representations
S112 outputting second ostomy representation
S112A storing the second ostomy representation
S112B transmitting with server device and/or receiving with accessory device the second ostomy representation
S112C displaying the second ostomy representation
200 accessory device
202 ostomy appliance
204 display
206 appliance image
208 server device
210 network
212 baseplate
214 adhesive surface
216 stomal opening
218 ostomy bag
220 output
250 appliance image of appliance image data
270 appliance image of transformed appliance image data
280 appliance image of appliance image data
301 memory module
302 processor module
302A image transformer
302B ostomy representation determiner
302C image representation determiner
303 wireless interface
401 memory module
402 processor module
402A image transformer
402B ostomy representation determiner
402C image representation determiner
403 interface
450 normal skin area
452 discoloured skin area
454 background
456 stoma
AID appliance image data
AID_T transformed appliance image data
AIR_1 first appliance image representation
AIR_2 second appliance image representation
AIR_3 third appliance image representation
AIR_4 fourth appliance image representation
BL_1 first boundary line
BL_2 second boundary line
BL_3 third boundary line
ID image data
ID_T transformed image data
IR_1 first image representation
IR_2 second image representation
IR_3 third image representation
IR_4 fourth image representation
OP_1 first ostomy parameter
OP_2_1 second primary ostomy parameter
OP_2_2 second secondary ostomy parameter
OP_2_3 second tertiary ostomy parameter
OP_2_4 second quaternary ostomy parameter
OR_1 first ostomy representation
OR_2 second ostomy representation
OR_3 third ostomy representation
SID stoma image data
SID_T transformed stoma image data
SIR_1 first stoma image representation
SIR_2 second stoma image representation
SIR_3 third stoma image representation
SIR_4 fourth stoma image representation

The invention claimed is:

1. A method for classifying an ostomy condition, the method comprising:
obtaining image data, the image data comprising stoma image data of a stomal area including a stoma and/or appliance image data of an adhesive surface of an ostomy appliance;
determining one or more image representations based on the image data, wherein the one or more image representations are binary masks that include a first pixel value indicating an association and a second pixel value indicating no association with the association indicated by the first pixel value;
determining one or more ostomy representations including a first ostomy parameter based on the one or more image representations; and
outputting the first ostomy parameter.

2. The method according to claim 1, wherein the one or more image representations comprises a stoma background image representation and/or an appliance background image representation, and wherein determining one or more ostomy representations is based on the stoma background image representation and/or the appliance background image representation.

3. The method according to claim 1, wherein the one or more image representations comprises a stoma image representation, and wherein determining one or more ostomy representations is based on the stoma image representation.

4. The method according to claim 1, wherein the one or more image representations comprises a first stoma discoloration representation, and wherein determining one or more ostomy representations is based on the first stoma discoloration representation.

5. The method according to claim 4, wherein the method comprises determining the first stoma discoloration representation based on red channel data of the image data.

6. The method according to claim 4, wherein the one or more image representations comprises a second stoma discoloration representation, and wherein determining one or more ostomy representations is based on the second stoma discoloration representation.

7. The method according to claim 6, wherein the method comprises determining the second stoma discoloration representation based on red channel data of the image data.

8. The method according to claim 1, wherein determining one or more image representations based on the image data comprises determining a base color parameter and determining the one or more image representations and/or the one or more ostomy representations based on the base color parameter.

9. The method according to claim 1, wherein the one or more image representations comprises a first appliance discoloration representation, and wherein determining one or more ostomy representations is based on the first appliance discoloration representation.

10. The method according to claim 9, wherein the one or more image representations comprises a second appliance discoloration representation, and wherein determining one or more ostomy representations is based on the second appliance discoloration representation.

11. The method according to claim 1, wherein the one or more image representations comprises an appliance area representation, and wherein determining one or more ostomy representations is based on the appliance area representation.

12. The method according to claim 1, wherein determining one or more ostomy representations comprises determining a first ostomy representation by combining a plurality of image representations.

13. The method according to claim 1, wherein the first ostomy parameter is a discoloration index indicative of discoloration of the stomal area.

14. The method according to claim 1, wherein the first ostomy parameter is a leakage parameter indicative of output distribution on the adhesive surface.

15. The method according to claim 1, the method comprising determining a first boundary line, based on the one or more image representations, and wherein an ostomy representation comprises the first boundary line.

16. The method according to claim 1, wherein determining one or more image representations based on the image data are performed by convolutional neural network with N layers in the range from 10-50 layers.

17. A system, comprising:
at least one processor; and
a memory storing instructions that, when executed by the at least one processor, cause the system to perform a set of operations, the set of operations comprising:
obtaining image data, the image data comprising stoma image data of a stomal area including a stoma and/or appliance image data of an adhesive surface of an ostomy appliance;
determining one or more image representations based on the image data, wherein the one or more image representations are binary masks that include a first pixel value indicating an association and a second pixel value indicating no association;
determining one or more ostomy representations including a first ostomy parameter based on the one or more image representations; and
outputting the first ostomy parameter.

18. The system of claim 17, wherein the one or more image representations comprises a stoma background image representation and/or an appliance background image representation, and wherein determining one or more ostomy representations is based on the stoma background image representation and/or the appliance background image representation.

19. The system of claim 17, wherein the one or more image representations comprises a stoma image representation, and wherein determining one or more ostomy representations is based on the stoma image representation.

20. The system of claim 17, wherein determining one or more image representations based on the image data comprises determining a base color parameter and determining the one or more image representations and/or the one or more ostomy representations based on the base color parameter.

* * * * *